United States Patent
Solimena et al.

(10) Patent No.: US 6,187,563 B1
(45) Date of Patent: Feb. 13, 2001

(54) βIV-SPECTRIN-POLYPEPTIDES AND NUCLEIC ACIDS ENCODING SAME

(75) Inventors: Michele Solimena, Hamden; Constance A. F. M. Berghs; Ronald A. Dirkx, Jr., both of New Haven, all of CT (US)

(73) Assignee: Yale University, New Haven, CT (US)

( * ) Notice: Under 35 U.S.C. 154(b), the term of this patent shall be extended for 0 days.

(21) Appl. No.: 09/368,590

(22) Filed: Aug. 4, 1999

Related U.S. Application Data

(60) Provisional application No. 60/095,657, filed on Aug. 7, 1998.

(51) Int. Cl.$^7$ .............................. C12P 21/06; C07H 21/04

(52) U.S. Cl. ......................................... 435/69.1; 536/23.5

(58) Field of Search ........................... 536/23.5; 435/69.1

(56) References Cited

U.S. PATENT DOCUMENTS

| | | |
|---|---|---|
| 3,791,932 | 2/1974 | Wilhelmus et al. . |
| 3,817,837 | 6/1974 | Rubestein et al. . |
| 3,839,153 | 10/1974 | Wilhelmus et al. . |
| 3,850,578 | 11/1974 | McConnell . |
| 3,850,752 | 11/1974 | Schuurs et al. . |
| 3,853,987 | 12/1974 | Dreyer . |
| 3,867,517 | 2/1975 | Ling . |
| 3,879,262 | 4/1975 | Schuurs et al. . |
| 3,901,654 | 8/1975 | Gross . |
| 3,925,074 | 12/1975 | Wyhof . |
| 3,984,533 | 10/1976 | Uzgiris . |
| 3,996,345 | 12/1976 | Ullman et al. . |
| 4,034,074 | 7/1977 | Miles . |
| 4,098,876 | 7/1978 | Piassio et al. . |
| 5,512,447 | 4/1996 | Baekkeskov et al. . |

OTHER PUBLICATIONS

Solimena, "Vesicular Autoantigens of Type 1 Diabetes", *Diabetes*, Metab. Rev. 14:227–240 (1998).

Ferro–Novick et al., "Vesicle fusion from yeast to man", *Nature* 370:191–193 (1994).

Martin, T. F., "The Molecular Machinery for Fast and Slow Neurosecretion", *Curr. Opin., Neurobiol.* 4:626–632 (1994).

Calakos, N. et al., "Synaptic Vesicle Biogenesis, Docking, and Fusion: A Molecular Description", *Physiol. Rev.* 76:1–29 (1996).

Greengard, F. et al., "Synaptic Vesicle Phosphoproteins and Regulation of Synaptic Function", *Science* 259:780–785 (1993).

Sorenson, R. L. et al., "Effect of Tyrosine Kinase Inhibitors on Islets of Langerhans: Evidence for Tyrosine Kinases in the Regulation of Insulin Secretion", *Endocrinal..* 134:1975–1978 (1994).

Hay, J. C. et al., "Resolution of Regulated Secretion into Sequential MgATP–dependent Calcium–dependent Stages Mediated by Distinct Cytosolic Proteins", *J. Cell. Biol.* 119:139–151 (1992).

Austin, C. D. et al., "Formation of Nascent Secretory Vesicles from the trans–Golgi Network of Endocrine Cells is Inhibited by Tyrosine Kinase and Phosphatase Inhibitors,", *J. Cell. Biol.* 135:1471–1483 (1996).

Cataldi, M. et al., "Protein–tyrosine Kinases Activate While Protien–tyrosine Phosphatses Inhibit L–type Calcium Channel Activity in Pituitary $GH_2$ Cells", *Biol. Chem.* 271:9441–9446 (1996).

Pang, D. T. et al., "Protein tyrosine phosphorylation in synaptic vesicles", *Proc. Natl. Acad. Sci. USA* 85:762–766 (1988).

Stenius, K. et al., "Structure of Synaptogyrin (p29) Defines Novel Synaptic Vesicle Protein", *J. Cell. Biol.* 131:1801–1809 (1995.

Parsons, S. J. et al., "$p60^{c-src}$ Activity Detected in the Chromaffin Granule Membrane", *Biochem. Biophys. Res. Comm.* 134:736–742 (1986).

Grandiori, C. et al., "$p60^{c-src}$ Is Complexed with a Cellular Protein in Subcellular Compartments Involved in Exocytosis", *J. Cell. Biol.* 107:2125–2135 (1988).

Burgoyne, R. D. et al., "Exocytosis in adrenal chromaffin cells", *J. Anat.* 183:309–314 (1993).

Sarafian, T. et al., "The Participation of Annexin II (Calpactin I) in Calcium–evoked Exocytosis Requires Protein Kinase C", *J. Cell Biol.* 114:1135–1147 (1991).

Hubaishy, I. et al., "Modulation of Annexin II Tetramer by Tyrosine Phosphorylation", *Biochemistry* 34:14527–14534 (1995).

Ferrer–Montiel, A. V. et al., "Tyrosine Phosphorylation Modulates the Activity of Clostridial Neurotoxins", *J. Biol. Chem.* 271:18322–18325 (1996).

Solimena, M. et al., "ICA 512, an autoantigen of type 1 diabetes, is an intrinsic membrane protein of neurosecretory granules", *EMBO J.* 15:2102–2114 (1996).

Rabin, D. U. et al., "Cloning and Expression of IDDM–Specific Human Autoantigens", *Diabetes* 41:183–186 (1992).

Rabin, D. U. et al., "Islet Cell Antigen 512 Is a Diabetes–Specific Islet Autoantigen Related to Protein Tyrosine Phosphatases", *J. Immunol.* 152:3183–3188 (1994).

Lan, M. S. et al.., "Molecular Cloning and Identification of a Receptor–Type Protein Tyrosine Phosphatase, 1A–2, from Human Insulinoma", *DNA Cell Biol.* 13:505–514 (1994).

(List continued on next page.)

*Primary Examiner*—Patrick Nolan
*Assistant Examiner*—Gerald R. Ewoldt
(74) *Attorney, Agent, or Firm*—Todd E. Garabedian; Wiggin & Dana

(57) ABSTRACT

The invention is directed to polypeptide or fragments thereof which interact with autoantigens of autoimmune diseases such as type I diabetes, and nucleic acid sequences which encode those polypeptide. The invention is also directed to methods for screening for autoimmune diseases such as type I diabetes, and methods and compositions for modulating hormone and neuropeptide secretion using proteins which interact with autoantigens of autoimmune diseases.

9 Claims, 49 Drawing Sheets

OTHER PUBLICATIONS

Strueli, M. et al., "Expression of the receptor–linked protein tyrosine phosphatase LAR: proteolytic cleavage and shedding of the Cam–like extracellular region", *EMBO J*, 11:897–907 (1992).

Serra–Pages, C. et al., "Mutational Analysis of Proprotein Processing, Subunit Association, and Shedding of the LAR Transmembrane Protein Tyrosine Phosphatase", *J. Biol. Chem.* 269:23632–23641 (1994).

Brady–Kalnay, S. M. et al., "Identification of the Homophilic Binding Site of the Receptor Protein Tyrosine Phosphatase PTPμ", *J. Biol. Chem.* 269:284722–28477 (1994).

Pulido, R. et al., "The LAR/PTPδ/PTPσ subfamily of transmembrane protien–tyrosine–phosphatases: Multiple human LAR, PTPδ, and PTP σ isoforms are expressed in a tissue–specific manner and associate with LAR–interacting protein LIP.1", *Proc. Natl. Acad. Sci. USA* 92:11686–11690 (1995).

Hermel et al., "Post–translational modifications of ICA512, a receptor tyrosine phosphatase–like protein of secretory granules", *Eur. J. Neurosci.* 11:20690 (1999).

Brady–Kulnay, S. M. et al., "Protein tyrosine phosphates as adhesion receptors", *Curr. Opin. Cell Biol.* 7:650–657 (1995).

Streuli, M. "Protein tyrosine phosphatases in signaling", *Curr. Opin. Cell Biol.* 8:182–188 (1996).

Passini, N. et al., "The 37/40–kilodalton autoantigen in insulin–dependent diabetes mellitus is the putative tyrosine phosphatase IA–2", *Proc. Natl. Acad. Sci. USA* 92:9412–9416 (1995).

Lu, J. et al., "Isolation, Sequence and Expression of A Novel Mouse Brain cDNA, mIA–2, And Its Relatedness To Members of the Protein Tyrosine Phosphatase Family", *Biochem. Biophys. Res. Comm.* 204:930–936 (1994).

Bult, A. et al., "STEP$_{61}$: A Member of a Family of Brain–Enriched PTP's Is Localized to the Endoplasmic Reticulum", *Neuroscience* 16:7821–7831 (1996).

Wasmeier, C. et al., "Molecular Clonong of Phogrin, a Protein–tyrosine Phosphatase Homologue Localized to Insulin Secretory Granule Membranes", *J. Biol. Chem.* 271:18161–18170 (1996).

Pietropaolo, M. et al., "Protein Tyrosine Phosphatase–Like Proteins: Link with IDDM", *Diabetes Care* 20:208–214 (1997).

Hatfield, E. C. , "Cross reactivity between IA–2 and phogrin/IA–2β in binding of autoantibodies in IDDM", *Diabetologia* 40:1327–1333 (1997).

Magistrelli, G. et al., "Expression of PTP35, The Murine Homologue Of The Protein Tyrosine Phosphatase–Related Sequence IA–2, Is Regulated During Cell Growth And Stimulated by Mitogens in 3T3 Fibroblasts", *Biochem. Biophys. Res. Chem.* 217:581–588 (1996).

Debant, Q. et al., "The multidomain protein Trio binds the LAR transmembrane tyrosine phosphatase, contains a protein kinase domain, and has separate rac–specific and rho–specific guanine nucleotide exchange factor domains", *Proc. Natl. Acad. Sci. USA* 93:5466–5471 (1996).

Haneji, N. et al., "Identification of α–Fodrin as a Candidate Autoantigen in Primary Sjogren's Syndrome", *Science* 276:604–607 (1997).

Yanagi, et al., "Anti–120–kDA α–fodrin immune response with Th1–cytokine profile in the NOD mouse model of Sjogren's syndrome", *Eur. J. Immunol.* 28:3336–3345 (1998).

Fields, D. et al., "A novel genetic system to detect protein–protein interactions", *Nature* 340:245–246(1989).

Vojtec et al., "Mammalian Ras Interacts Directly with the Serine/Threonine Kinase Raf", *Cell*, 74:205–214 (1993).

Gluzman, "SV40–Transformed Simian Cells Support the Replication of Early SV40 Mutants", *Cell*, 23:175–182 (1981).

Chen et al., "High–Efficiency Transformation of Mammilian Cells by Plasmid DNA", *Molecular and Cellular Biology*, 7:2745–2752 (1987).

Hanson et al., "Expression of a Multifunctionsl $^{Ca2+}$/Calmodulin–Dependent Protein Kinase and Mutational Analysis of Its Autoregulation", *Nueron*, 3:59–70 (1989).

Altschul et al., "Protein database searches for multiple alignments", *Proc. Natl. Acad. Sci. USA* 87:5509–5513 (1990).

Pawson, T., "Protein modules and signalling networks", *Nature* 373:573–580 (1995).

Huse et al., "Generation of a Large Combinational Library of the Immunglobulin Repertoire in Phage Lambada", *Science* 246:1275–1281 (1989).

Bradley–Mullen, "Activation of Distinct Subsets of T Suppressor Cells with Type III Pneumococcal Polysaccharide Coupled to Syngeneic Spleen Cells", in *Immunological Tolerance to Self and Non–Self*, Buttisto et al., eds. Annals, N.Y. Acad. Sci., vol. 392, pp. 156–166 (1982).

Hu et al. Characterization of Human Brain cDNA Encoding the General Isoform of B–Spectrin. JBC 267, 26:18715–18722, Sep. 15, 1992.*

Paulsen et al. Characterization of Sin, A Potential Recombinase–Encoding Gene From *Satph. A*. Gene 141:109–114, 1994.*

Berghs et al. Identification of Graspin 204.10 Society for Neuroscience Abstracts., Nov. 7, 1998.*

Asakawa et al. Human Brain BAC Library: Construction & Screening. Gene 191: 69–79, May 1997.*

* cited by examiner

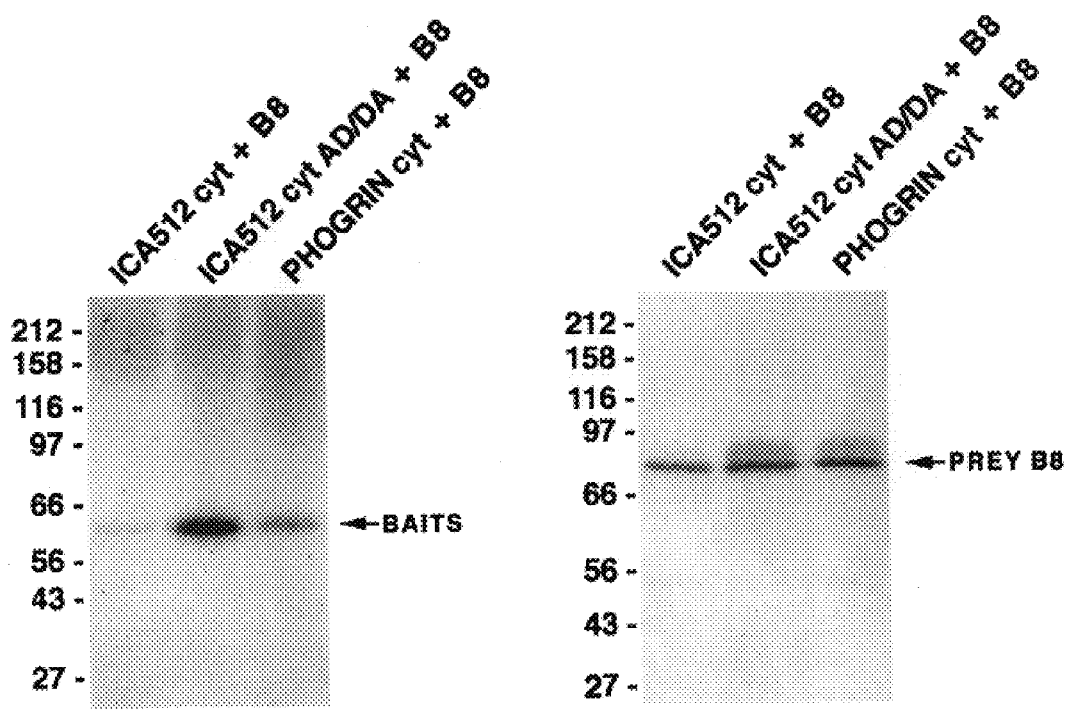

```
CTACTGGTCTCTTTCTACCACTATTTCTCCAAGATGAAAGCCTCTGGCTGTGGAGGGGAAAGCCGTATCGG
                                                                      70
                     ├── spectrin repeat 1 ─────────────────────────────
  L  L  V  S  F  Y  H  Y  F  S  K  M  K  A  L  A  V  E  G  K  A  V  S
├ actin-binding ([) ┤
GAAGGGCCTGGATCCACCGCACCGTGGGCYTCATCAGCAATCAGAAATTTGCCAACTCCTTAAGTGGGGT
                                                                     140
  ──────────────── spectrin repeat 1 ──────────────┤
  G  R  A  W  I  H  R  T  V  G  ?  I  S  N  Q  K  F  A  N  S  L  S  G  V GCAGCAGCAACTCCAGGCTTTCACGGCCTATTGCACGCTGGAGAAGCCTGTCAAGTTCCAGGAGAAGGGG
                                                                     210
                  ├── spectrin repeat 1 ──────────────────────────────
  Q  Q  Q  L  Q  A  F  T  A  Y  C  T  L  E  K  P  V  K  F  Q  E  K  G AACCTAGAGGTGCTCTTCAGCATCCAGAGCAAACTGCTGCCTGCAACCGTCGCCTCTTTGTGCCTC
                                                                 280

FIG.5A
```

FIG. 5B spectrin repeat 1

N L E V L L F S I Q S K L R A C N R R L F V P
GGGAGGGCTGTGGCATCTGGGATATTGACAAGGCATGGGGTGAGCTGAGCATGAGCGGGA
350 spectrin repeat 2

R E G C G I W D I D K A W G E L E K A E H E R E
GGCTGCCCTACGGGCTGAGCTGATTCGGCAGGAGAAGCTGAACTACTGGCCACAGAGGTTTGACCACAAG
420 spectrin repeat 2

A A L R A E L I R Q E K L E L L A Q R F D H K

```
GTGGCTATGAGGGAGAGCTGGCTGAATGAGAACCAGCGTCTCTGGTCTCCCAGGACAACTTTGGGTATGAGC
                                                                                    490
                        ━━━━━━━ spectrin repeat 2 ━━━━━━━
 V   A  M  R  E  S  W  L  N  E  N  Q  R  L  V  S  Q  D  N  F  G  Y  E TGCCCGCAGTGGAGGCAGCCATGAAGAAACACGAAGCCATCGAGGCAGACATTGCGGCCTACGAGGAGCG
                                                                                    560
                                ━━━━━━━ spectrin repeat 2 ━━━━━━━
 L  P  A  V  E  A  A  M  K  K  H  E  A  I  E  A  D  I  A  A  Y  E  E  R GGTGCAGGGTGTGGCGGAGCTGGCCCAGGCATTGGCCAGCCGAAGGCTACTACGATATCCGGCGGGTGGCA
                                                                                    630
                                               ━━━━━ ⫫ spectrin ━━━
 V  Q  G  V  A  E  L  A  Q  A  L  A  A  E  G  Y  Y  Y  D  I  R  R  V  A GCCCAGGCGTGACAGCCGTCCTGCGCCAGTGCCCTGCTAACTGGGCCCTTGTGGGTGCCCGGGGACACGAC
                                                                                    700
```

```
A Q R D S V L R Q W A L L T G L V G A R R T R
                                              spectrin repeat 3
TTGAGCAGAACCTTGCCCTGCAGAGATGGTGTACATGGTGGACTGGATGGAGGAGAT
                                                           770

L E Q N L A L Q K V F Q E M V Y M V D W M E E M
                                              spectrin repeat 3
GCAGGCTCAGCTGCTGTCCCGGGAGTGTGGGCAGCACCTGGTGGAGGCAGACGACCTGTTGCAGAAGCAT
                                                                     840

Q A Q L L S R E C G Q H L V E A D D L L Q K H
                                              spectrin repeat 3
```

FIG. 5E spectrin repeat 4

L E E A E S W A R D K E R L L E A A G G G G A

CGGGCGCAGCGGGGGCAGCGGGAACAGCGGCGGGCGCGCATGACCTGTCCAGCACAGCGCCTCCTGGC

1190 spectrin repeat 4

A G A A G A A G T A G G A H D L S S T A R L L A

CCAGCACAAGATCCTGCAGGGCTGGGGCGAGCTGCTGGGCGGCGTCGCTGCAGCAGGCCCTGCGGTGTGGC

1260 spectrin repeat 4

GAGGAGCTGGTTGCGGCCGGGGCCGTGCCCGGGGAGCCCGGGGAGCAGACACCGTGCACCTGGTAGGCCTGGCGG
                                                                              1330

■━━━━━ spectrin repeat 4 ━━━━━■  ■ spectrin
 E  E  L  V  A  A  G  G  A  V  G  P  G  A  D  T  V  H  L  V  G  L  A AGCCGCGGCGGAGCGCCGGCCCGGCTGGCAGAGAGGCTGGAAGAGGCCGCGGCGAGAGCGGCGGCT
                                                                              1400

■━━━━━ spectrin repeat 5 ━━━━━■
 E  R  A  A  S  A  R  R  R  W  Q  R  L  E  E  A  A  A  R  R  E  R  L GCAGGAGGCGGCCGCGCTGCACCAGTTCGGGGCGCTGACCTTCGACGGGCTGCTGGACTGGCTTCGGGACGCT
                                                                              1470

■━━━━━ spectrin repeat 5 ━━━━━■
 Q  E  A  R  A  L  H  Q  F  G  A  D  L  D  G  L  L  D  W  L  R  D  A TACCGCCTGGCAGCCCGCCGGTGACTTCGGCCACGACGAAGCTTCCAGCCGCCTGGGCGCCGCCAGCACC
                                                                              1540

FIG.5G spectrin repeat 5

Y R L A A A G D F G H D E A S S R R L A R Q H
GCGCGCTCACCGGGAGGTGGAGGCACATCGCGGGCCCGTGAGGCGGCCTGCGCCAGCTGGCGACACT
1610 spectrin repeat 5

R A L T G E V E A H R G P V S G L R R Q L A T L
CGGGGGTGCCAGTGGGCCACTGGTGGGCGCTGCAGGTTGGGCGTTGCTGCAGGTTGTGAAGCAGAGCAGTTG
1680 spectrin repeat 5 ——— spectrin repeat 6

```
TTCGCTGAGGTGACCGAAGTGGCGGCGCTGAGGCGCCAGTGGCTGCGGGACGCGCTCGCTGTCTACCGCA
                                                                      1750
━━━━━━━━━━━ spectrin repeat 6 ━━━━━━━━━━━
 F  A  E  V  T  E  V  A  A  L  R  R  Q  W  L  R  D  A  L  A  V  Y  R TGTTTGGCGAGGTGCACGCGTGTGAGCTGTGTGGATCGGCGAGAAGGAGCAATGGCTGCTCTCCATGCGTGT
                                                                       1820
━━━━━━━━━━━ spectrin repeat 6 ━━━━━━━━━━━
 M  F  G  E  V  H  A  C  E  L  W  I  G  E  K  E  Q  W  L  L  S  M  R  V GCCGGATTCACTCGACGACGTCGAGGTGGTGCAGCACCGATTCGAGAGCCTGGACCAAGAGATGAACAGC
                                                                     1890
━━━━━━━━━━━ spectrin repeat 6 ━━━━━━━━━━━
 P  D  S  L  D  D  V  E  V  V  Q  H  R  F  E  S  L  D  Q  E  M  N  S CTGATGGGCCGTTCTGGACGTGAACCACAGTCCAGGAGCTGGTGGAAGGAGGCCACCCCAGTTCAG
                                                                  1960
```

FIG. 51 spectrin repeat 6

L M G R V L D V N H T V Q E L V E G G H P S S
ATGAGGTGCGTTCCTGCCAGGACCACCTCAACAGCAGGTGGAGCTAGTGGAACAGCG
                                                    2030 spectrin repeat 7

D E V R S C Q D H L N S R W N R I V E L V E Q R
CAAAGAGGAAATGAGCCGGGTGCTGCTGGTGGAGAACCACGTGCTCGAGGTGGCCGAGGTGCGCGCCCAG
                                                    2100 spectrin repeat 7

FIG.5K spectrin repeat 8
L A S A A Q A C G E A V A A A G R L Q R F L H
ACCTCGACGCTTTCCTGGACTGGCTCGTGCGCCCCAGGAGGCGGCGGCGGGGAGGGGCCCCTGCC
2450 spectrin repeat 8
D L D A F L D W L V R A Q E A A G G S E G P L P
CAACAGCCTAGAAGAAGCGGCGGACGCGCTGCTGCCACGCTGCGCTCAAGGAGGAGGTGGACCAGCGC
2520 spectrin repeat 8
N S L E E A D A L L A R H A A L K E E V D Q R

FIG.5L

GAGGAAGACTATGCTCGCATCGTGGCGGCCAGCGAGGCGCTGCTGGCCGCCGACGGCGCAGAGCTGGGCC
———————————— spectrin repeat 8 ————————————
E  E  D  Y  A  R  I  V  A  A  S  E  A  L  L  A  A  D  G  A  E  L  G

2590

CGGGCCTGGCACTAGACGAGTGGCTGCCACACCTCGAACTTGGCTGGCATAAACTGCTCGGCTTGTGGAA
———————————— spectrin repeat 9 ————————————
P  G  L  A  L  D  E  W  L  P  H  L  E  L  G  W  H  K  L  L  G  L  W  K
spect

2660

GGCGGCGCAGGAAGGCGTGGTCCAGGGCGCACATCTACCAGCTCTTCCTGCGGGATCTACGCCAGGGCTC
———————————— spectrin repeat 9 ————————————
A  R  R  K  A  L  V  Q  A  H  I  Y  Q  L  F  L  R  D  L  R  Q  A  L

2730

GTGGTGCTGCGTAACCAGGAGATGGGCGCTGTCTGGTGCGAGCTCCCGGGCACAGTGGAATCGGTGGAGG

FIG. 5N spectrin repeat 9
V V L R N Q E M A L S G A E L P G T V E S V E
AGGCCTTGAAACAGCACCGTGACTTTCTCACCACCATGGAGCTGAGCCAGCAAAAGATGCAGGTGGCCGT  2870 spectrin repeat 9
E A L K Q H R D F L T T M E L S Q Q K M Q V A V
GCAGGCTGCAGAGGGCCTGCTGAGGCAGGGCAACATCTACGGGGAGCAGGCTCAGGAGGCTGTGACCCGG  2940 spectrin repeat 9        spectrin repeat 10
Q A A E G L L R Q G N I Y G E Q A Q E A V T R CTGCTGGAGAAGAACCAAGAAAACCAGTTACGGGCCCAGCAATGGATGCAAAAGCTACATGACCAACTTG
―――――――――――――――― spectrin repeat 10 ――――――――――――――――
L L E K N Q E N Q L R A Q Q W M Q K L H D Q L AGCTGCAGCACTTCCTCCGAGACTGCCACGAGCTGGATGGCTGGATCCATGAGAAGATGCTGATGGCGCG
―――――――――――――――― spectrin repeat 10 ――――――――――――――――
E L Q H F L R D C H E L D G W I H E K M L M A R GGATGGCACGCGGGAGGACAACCACAAGCTGCATAAGAGAGATGGCTCCGGCACCAGGCATTCATGGCCGAG
―――――――――――――――― spectrin repeat 10 ――――――――――――――――
D G T R E D N H K L H K R W L R H Q A F M A E

CTGGCTCAGAATAAGGAGTGGCTGGAGAAGATCGAGCGGGAGGGCCCAGCAACTGATGCAGGAGAAGCCC

3010

3080

3150

3220

FIG.50 spectrin repeat 10 ━━━━━━━━━━━━

L A Q N K E W L E K I E R E G P A T D A G E A
GAACTGGGCGGCCTCCGTGCTGGGAGAAGAAGCTGGGGAGATCCGCGCCAGTGCTGGGGAGAGCACCA
                                                                3290 spectrin repeat 11 ━━━━━━━━━━━━
spectrin repeat 1 ▬

R T G G L R A E E E A G R D P P V L G G A G E H H
CCCAGGCCCAAGGCACGGGCAGCTCTTTGAGGCCCAGCAAAGCAGACCAGCTGGTGCAGAGCTTTGCTGAG
                                                                    3360 spectrin repeat 11 ━━━━━━━━━━━━

```
CTGGACAAGAAGCTCCTTCACATGGAGAGCCAGCTGCAAGACGTGGACCCTGGAGGAGACCTGGCCACTG
                                                                            3430
━━━━━━━━━ spectrin repeat 11 ━━━━━━━━━
 L  D  K  K  L  L  H  M  E  S  Q  L  Q  D  V  D  P  G  G  D  L  A  T TCAACAGTTCAGCTCAAGAAGCTGCAGTCCATGGAGAGTCCAGGTGGAGGAGTGGTACCGCGAGGTGGGAGA
                                                                            3500
━━━━━━━━━ spectrin repeat 11 ━━━━━━━━━
 V  N  S  Q  L  K  K  L  Q  S  M  E  S  Q  V  E  E  W  Y  R  E  V  G  E GCTGCAGGGCGCAGAACGGGCTGCCCGCTGGAGCAAGGAGCTGGTGGGTGAGGGCAGAAC
                                                                            3570
━━━━━━━━━ spectrin repeat 11 ━━━━━━━━━
 L  Q  A  Q  T  A  A  L  P  L  E  P  A  S  K  E  L  V  G  E  R  Q  N GCGGTGGGCGAGCGCCTGGTGCCGCTCGAGCCGTTGCAGGAGGCCGCCTTGCTGCTGCTTCCA
                                                                            3640
```

FIG.5Q

```
─ spectrin repeat 12 ─
  A  V  G  E  R  L  V  R  L  L  E  P  L  Q  E  R  R  R  L  L  L  A  S
  AGGAGTTGCACCAGGTTGGCCGCACGACCTGGAGACGAGCTGGCATGGGTTCAGGAGCGGCTGCCACTGGC
                                                                    3710
─ spectrin repeat 12 ─
  K  E  L  H  Q  V  A  H  D  L  D  D  E  L  A  W  V  Q  E  R  L  P  L  A
  CATGCAGACAGAGGCCGAGGCAACGGTTTGCAGGCACAGCAGCACATCAAAAAGAACCAGGGCCTGCGG
                                                                    3780
─ spectrin repeat 12 ─
  M  Q  T  E  R  G  N  G  L  Q  A  V  Q  Q  H  I  K  K  N  Q  G  L  R
```

FIG. 5R

CGGGAGATCCAGGGGCATGGGCCCGCGCCTGGAGGAGGTGCTGGAGCGCGCGGGCGCTGGCGCTGCGCTGC 3850

R E I Q A H G P R L E E V L E R A G A L A S L

———— spectrin repeat 12 ————

GCAGCCCGGAGGCAGAGGCAGTGCGCCGGGGCCTGGAGCAGCTGCAGAGCGCCTGGGCCGGACTGCGGGA 3920

R S P E A E A V R R G L E Q L Q S A W A G L R E

———— spectrin repeat 12 ————  ———— spectrin repeat 13 ————

GGCTGCCGAGCGCCGACGGCAGGCAGGTGCTGGACGCCGCCTTCCAGGTGGAGCAGTACTACTTCGACGTGGCT 3990

A A E R R Q Q V L D A A F Q V E Q Y Y F D V A

———— spectrin repeat 13 ————

GAGGTGGAGGGCGTTGGGCTGGGCGAGCAGGAGCAGCTGCTCATGATGATGAGGACAAGGGCAAGGTGCGCCCGA 4060

FIG.5S spectrin repeat 13
E V E A W L G E Q E L L M M S E D K G K V R P
GCTGGGGGTGGAGGGCCTGGGGCTGCTCATGATGAGCGAGGACAAGGGCAAGGTGCGGCCT
4130 spectrin repeat 13
S W G C G G P G G A G A G G R R R C R L I V G A L
GTGCCCCCAGGACGAGAACAGAGAGCACCCTGCAGCTGCTCAAGAAACACCTGCAGCTGGAGCAGGGCGTGGAG
4200 spectrin repeat 13
C P Q D E Q S T L Q L L K K H L Q L E Q G V E

FIG. 5T

```
AACTACGAGGAAAGCATCGCGGCAGTGCCGGCCTGTCGCGCCAGTGCCGGCCTGTGCGAGATGGGGCACCCGGACA
                                                                            4270
         ━━━━━━━━━ spectrin repeat 13 ━━━━━━━━━
 N  Y  E  E  S  I  A  Q  L  S  R  Q  C  R  A  L  L  E  M  G  H  P  D GCCGAGCAGATCAGCCGGCGGCAGTCTCAGGTGGACCGCCTGTACGTGGCGCTCAAGGAGCTGGGTGAGGA
                                                                        4340
        ━━━━━━━━━ spectrin repeat 14 ━━━━━━━━━
 S  E  Q  I  S  R  R  Q  S  Q  V  D  R  L  Y  V  A  L  K  E  L  G  E  E GCGCCCGGGTGGCCTCTGGAACAGCAGTACTGGCTGTACCAGCTTCAGCCGCCAGGTGAGCGAGCTTGAGCAC
                                                                         4410
                     ━━━━━━━━━ spectrin repeat 14 ━━━━━━━━━
 R  R  V  A  L  E  Q  Q  Y  W  L  Y  Q  L  S  R  Q  V  S  E  L  E  H TGGATTGCCGAGAAGGAGGTGGTGGCTCACCCGAGCTCGGCCAGGACTTTGAGCATGTCTCGGTGC
                                                                   4480
```

```
                      spectrin repeat 14
 W  I  A  E  K  E  V  V  A  G  S  P  E  L  G  Q  D  F  E  H  V  S  V
TGCAGGAGAAATTCTCAGAGTTTGCCAGCGAGACAGGTATGGCAGGGCGGGAACGGCTGGCAGCTGTGAA  4550
                      spectrin repeat 14
 L  Q  E  K  F  S  E  F  A  S  E  T  G  M  A  G  R  E  R  L  A  A  V  N
CCAGATGGTGGATGAGCTGATCGAGTGTGGCCATACAGCAGCGGCCACCATGGCCGAGTGGAAGGACGGA  4620
                      spectrin repeat 14           spectrin repeat 15
 Q  M  V  D  E  L  I  E  C  G  H  T  A  A  A  T  M  A  E  W  K  D  G
```

CTGAACGAGGCCTGGGCTGCTGAGCTCATGGGCACACGGGCCCAGCTGCTGGCCGCCTCTCGGG 4690

L N E A W A E L L E L M G T R A Q L L A A S R
spectrin repeat 15

AGCTTCATAAGTTCTTCAGTGACGCCCGAGAGCTTCAGGGACAGATTGAGGAGAAGCGGAGGGGCTGCC 4760

E L H K F F S D A R E L Q G Q I E E K R R R L P
spectrin repeat 15

CCGCCCTGACCACCCCGCCTGAGCCCCGAGACCCAGTTCCATGCAGCGGACCCTGAGAGCCTTTGAG 4830

R L T T P P E P R P S A S S M Q R T L R A F E
spectrin repeat 15

CATGACCTGCAGCTCCTCGTGTCCCAGGTACGGCAGCTGCAGGAGGGGCGGCCCAGCTGCGGACGGTGT 4900

FIG.5W

H D L Q L L V S Q V R Q L Q E G A A Q L R T V
ATGCGGGTGAACATGCCGAGGCCATCGCTAGCCGGGAGCAGGAGGTGCTGCAGGGTTGGAAAGAGCTGCT
— spectrin repeat 15 —
— spectrin repeat 16 —
4970

Y A G E H A E A I A S R E Q E V L Q G W K E L L
GTCAGCCTGTGAGGATGCCGCCTGCATGTCAGCTTCCACAGCCCTGCGCTTCCACAGCCAAGTC
— spectrin repeat 16 —
5040

```
CGCGACCTGCTCTCCTGGATGGACGGCATCGCCAGCCAGATTGGGGCAGCCGACAAGCCCAGGGACGTGT  5110
                    ─── spectrin repeat 16 ───
 R  D  L  L  S  W  M  D  G  I  A  S  Q  I  G  A  A  D  K  P  R  D  V CATCAGTGGAGGTGCTCATGAACTACCACCAGGGCCTGAAGACTGAGCTGGAGGCGCGGGTGCCTGAGCT  5180
                    ─── spectrin repeat 16 ───
 S  S  V  E  V  L  M  N  Y  H  Q  G  L  K  T  E  L  E  A  R  V  P  E  L GACCACCTGCCAGGAGCTGGGGCGATCTCTGCTGCTCAACAAAAGTGCCATGGCTGATGAGATCCAGGCA  5250
                                           ─┤ spectrin re─
 T  T  C  Q  E  L  G  R  S  L  L  L  N  K  S  A  M  A  D  E  I  Q  A

CAGCTGGACAAGCTGGGAACCAGGAAGAGGAGGTGTCGGAAAAGTGGGACCGCCATTGGGAGTGGCTGC  5320

FIG.5Y
``` spectrin repeat 17

Q L D K L G T R K E E V S E K W D R H W E W L
AGCAGAGATGCTGGAGGTGCACCAGTTTGCCCAGGAGGCGGTGGTGGCTGATGCTGGCTGACAGCCCAGGA 5390 spectrin repeat 17

Q Q M L E V H Q F A Q E A V V A D A W L T A Q E
GCCGCTCCTGCAGAGAGCCCGGGGAGCTGGGACAGCAGCGTGGATGAGGTGGAGCAGCTTATCCGGGCGACATGAG 5460 spectrin repeat 17 clone B8

GCCTTCCGCAAAGCGGGCTGCAGCCTGGGAAGAGAGGTTCAGCTCTCTGCGGCCTGACCACGATCGAGA 5530

─── spectrin repeat 17 ───
─── clone B8 ───

A  F  R  K  A  A  A  A  W  E  E  R  F  S  S  L  R  R  L  T  T  I  E

AAATCAAAGCGGAACAGAGCAAGCAGCCGCCTACCCCACTGCTGGGGCGCAAGTTCTTTGGGGACCCCAC 5600

─── spectrin repeat 17 ───
─── clone B8 ───

K  I  K  A  E  Q  S  K  Q  P  P  T  P  L  L  G  R  K  F  F  G  D  P  T

GGAACTGGGGCCAAGGCCGGCCCCTGCTGCCGGGCCAGGGGGCTATGAAAGGGGCTTGGAGCCCCTGGCC 5670

FIG.5A-1 clone B8

E L A A K A K A A P L L R P G G Y E R G L E P L A
CGCCGAGCCTCGGACACGCTCTCGGCCCGAGGTGCGCCAGGACTCGGGGTATGTGCGCCAGGAGCTCAAGC
                                                                    5740 clone B8

R R A S D T L S A E V R T R T R V G Y V R Q E L K
CCGAGCGGCCTCCAGCCGCCATTGACCGGAGATCCCGGGGAGGTGAGCCCGGCCCTGCC
                                                         5810 clone B8

```
GGCCGGCACCAGAGGACGCCGGCGACCCCGGCGGGAGCAGGTGCGGCCACGACCG     5880
            |---------clone B8----------------------|
             A  A  P  E  D  A  A  A  E  T  P  A  T  P  A  A  A  E  Q  V  R  R  P GAGCGCCAGGAGTCAGCTGATCGCGGCTGCCCAGGAGGCTGAGCGGGCCTGAGCGGCAAGAGTCAG     5950
           |-BIV repeat 1-|                        |-BIV repeat 2-|

E  R  Q  E  S  A  D  R  A  E  E  L  P  R  R  R  R  P  E  R  Q  E  S
            |--------------------clone B8---------------------|

TCGATCAATCCGAGGAGGCTGCGCGGAGGCGGCCGAGCGGCAGGAGTCAGCGGGAGCACGAGGGGGC     6020
```

FIG.5C-1

```
                    BIV repeat 3
                  ┌──────────────┐
 clone B8 ─────────────────────────────────────────────────────────

V  D  Q  S  E  E  A  A  R  R  R  R  R  P  E  R  Q  E  S  A  E  H  E  A  A
  ACACAGCCTTACCCTGGGCCGCTATGAGCAGATGGAGCGGCGCGAGCGGCGTGAGCGGCGCTTGGAG
                                                                     6090
                                                              [BI■]
 clone B8 ─────────────────────────────────────────────────────────

H  S  L  T  L  G  R  Y  E  Q  M  E  R  R  R  R  E  R  R  R  L  E
  CGGCAGGAGTCCAGCGAACAGGAGATGCCCATCAGAGGAGACCTGGTCAAGGGGAAGGCCACCCTGGCTG
                                                                     6160
                  BIV repeat 4
                  ┌──────────────┐
 clone B8 ─────────────────────────────────────────────────────────

```
ACATTGTGGAACAGCTGCAGGAGAAAGAGGCAGGCCCAGGGCTGCCTGCTGGGCCGTCGCTGCCTCAGCC   6230
                    ─────────────────────clone B8──────────────────────
 D  I  V  E  Q  L  Q  E  K  E  A  G  P  G  L  P  A  G  P  S  L  P  Q  P ACGGCGAGCTTCCCCCAGGTCGCCTGCCCCAACGGGCTTGAGCTGCCCGAGCGGACACCTCGGCCGGACCGG   6300
                    ─────────────────────clone B8──────────────────────
 R  E  L  P  P  G  R  L  P  N  G  L  E  L  P  E  R  T  P  R  P  D  R CCCCGGGGCGCGGGACCGGCCCAAGCCGCGGCGACGGCCGCGCCCAGAGAGGGTGGTGAGGGCGGGGGAA   6370
                    ─────────────────────clone B8──────────────────────
 P  R  A  R  D  R  P  K  P  R  R  R  R  P  R  R  E  G  G  E  G  G  G

GCCGGGGCGGCTCCGCTTCCGCCTCGGGCCCCAGGGCCCCGCTCCGCCGCTCCGCCACCGCCCACTCACAC   6440

FIG.5E-1
```

TGGGTGAGCCTGTACTGTGTGCTTAGTAAGGGGGAACTGGGCTTCTACAAGGACTCCAAGGGCCCGGCAT — 6580

PH domain clone B8

W V S L Y C V L S K G E L G F Y K D S K G P A

CCGGGAGCACACGGTGGGGAACCGCTGCTCAGCCTGCACAAGGCCACCAGCGAGGTGGCTAGTGACTA — 6650

PH domain clone B8

S G S T H G G E P L L S L H K A T S E V A S D Y

CAAGAAAAAGAAGCATGTCTTCAAGCTCCAGACCCAGGATGGCAGTGAGTTTTTGCTCCAGGCAAAAGAT — 6720

FIG.5G-1

PH domain clone B8

K K K K H V F K L Q T Q D D G S E F L L Q A K D

GAGGAGGAGATGAACGGCTGGCTGGAGGCTGTAGCTTCCTCGGTGGCGAACACGCAGAGATCGCCCGCT
6790

PH domain clone B8

GGGGCCAGAGACACTACCCACTACTTCATCCACAGATGAGGGCAACCCTAAGAGGGAAGGGCGGAGATCGCAG 6860

─── PH domain
── clone B8

W G Q T L P T T S S T D E G N P K R E G G D R R

GGCCAGGCGGGGCGGCAGGAAGTGACTTCCCACCCCAGGACCTGACACATCGTCTCCCCTCTTTTCCGCA 6930

■── PH domain
── clone B8

A S G R R K L P T P R T H I S S P L F S A

CTGTGGGCACAAAGACACTTTTCTTCCGCAGGGGCGGGAGCCCCTAGTTCCAACACTGAGGACGGCGTGA 7000

FIG.51-1 clone B8

L W A Q R H F F F R R G G S P F Q H G R V
CATGGTGGGCACCGGAAAGGAGGGACTTCTCCTGCACCCCAAGAAGTGGTGGGAGATTGCTGCCCTA
                                                              7070 clone B8

T W W A P E R R G L L L H P K K W G D C C P Y
TAGCCATATCTCGGCCCCTTCCCACTCACCACCCCCACCCCCAGGTGCTGGGGGTCCCTTATTTTATGCA
                                                                7140 clone B8

```
ATAACTGAGCTTGATGGGGTGGGCCAGGCAAGGGGCCAGTTGAGCCAAGCCCCCAGCCCGATCTGCAGATCCT
                                                                          7210
————————————————————————— clone B8 —————————————————————————
  I   T   E   L   D   G   G   G   Q   G   A   S       A   K   P   P   A   P   I   C   R   S GCCCCAAGAAGCTGGGGTGGTGGGGCAGTAATTCCTGCCCCCTCTCTGCCCTAGGGATGGGCACGGGG
                                                                        7280
————————————————————————— clone B8 —————————————————————————
  C   P   K   K   L   G   W   W   G   Q       F   L   P   P   S   L   P       G   W   A   R   G GCGCTGGTGAGGTCCCCTGGACCATCCAGGGTGCTAGGGGCAGGGAGGGACACCCCTCCCGCCTTT
                                                                    7350
————————————————————————— clone B8 —————————————————————————
  R   W   .   G   P   L   D   H   P   G   C       G   A   G   R   G   H   P   L   P   A   F ACCTCACTTCCAATGCTGCCTTGATCTCTGTCTGGGAGGGAGTGAAGGGGCCCTAGCCCCCTGCACT
                                                                      7420
```

FIG.5K-1 clone B8

T  S  L  P  M  L  P      S  L  S  G  R  G  E      R  G  P  S  P  L  H

CCGCCGCCTCAGAGCCATGCGGTTAATTCCTGACTTAGTTTATTTTTGCAAAACGTCGATCTCCCTCC
                                                                          7490 clone B8

S  A  A  S  E  P  C  G      F  L  T      F  I  F  A  K  R  R  S  P  P  P

CCCGCCCCGCATCCGCGGAAGGCTTTTAATGGGAGGGGCGTCAAAGCTCAAAACTGTTTCCTCTCCCTC
                                                                          7560 clone B8

```
CCCCCTCCAGTTGTAAATGCCACTTCATGAGGGAGGGCGAGGGAAGCCCACCCCTGCATGCTTCTGG
                                                                    7630
               clone B8
 P  P  P  V  V  N  A  T  S  G  E  G  R  G  E  A  H  P  C  M  L  L CTGGAGCACCTCCCTGGGGAGTCGGGGGATTGGGTTGTGGGCAGTCCCCATGCCGCCTGGAGAAGCCGC
                                                                    7700
               clone B8
 A  G  A  P  P  W  G  V  G  G  L  G  C  G  Q  S  P  W  P  P  G  E  A  A TGGGGCCCGGGGGGTGTGGGGCGTGTGGGGGTGTACCTATATAAACCCTTTGGCTTT
                                                          7770
               clone B8                       ⊢pAS⊣
 G  A  R  G  C  G  A  V  W  R  A  H  T  V  C  T  Y  N  K  P  F GAAAAAAAAAAAAAAAAAAAAAAAAAAAAAAA 7812
               clone B8
 E  K  K  K  K  K  K  K  K  K  K  K  K  K  K  K

FIG.5M-1
```

βIV-SPECTRIN-POLYPEPTIDES AND NUCLEIC ACIDS ENCODING SAME

This application claims the benefit of U.S. Provisional Patent Application No. 60/095,657 filed Aug. 7, 1998.

STATEMENT OF GOVERNMENT SUPPORT

This invention was made in part with government support under grant numbers NIH-NIDDK 53022 and NIH-NIDDK 54913 from the National Institutes of Health. The government has certain rights in this invention.

BACKGROUND OF THE INVENTION

1. Field of the Invention

This invention relates to proteins, polypeptides, or fragments thereof, which interact with autoantigens of autoimmune diseases, such as type I diabetes. More particularly the invention relates to polypeptides, or fragments thereof, which interact with human ICA512 and phogrin. The invention also relates to nucleic acid sequences which encode these polypeptide or polypeptide fragments. The invention also relates to methods for identifying and treating individuals who suffer from or are susceptible to diabetes, screening for autoimmune diseases such as type I diabetes, and modulating hormone and neuropeptide secretion using proteins or protein fragments which interact with autoantigens of autoimmune diseases.

2. Description of the Related Art

Insulin dependent diabetes mellitus (also known as IDDM or type I diabetes) primarily afflicts young people. Although insulin is available for treatment, the several-fold increased morbidity and mortality associated with this disease urge the development of early diagnostic and preventive methods. The destruction of pancreatic β-cells, which precedes the clinical onset of IDDM, is mediated by autoimmune mechanisms. Among the most thoroughly studied autoimmune abnormalities associated with the disease is the high increase of circulating β-cell-specific autoantibodies at the time of diagnosis.

A major goal of diabetes research has been to develop immune interventions that block or inhibit the destruction of β-cells and development of IDDM. For example, U.S. Pat. No. 5,512,447, the disclosure of which is incorporated herein by reference, describes assays for the detection of diabetes and prediabetic status by exposing patient serum samples to purified ligand capable of binding autoantibodies specific for a 64 kD autoantigen present in pancreatic β-cells. One of the most intriguing observations resulting from studying the cell biology of β-cell autoantigens is that all major targets of IDDM autoantibodies identified thus far are directly connected with the secretory apparatus of β-cells (Solimena, Diabetes, Metab. Rev. 14:227–240 (1994)).

A large body of evidence indicates that protein and lipid phosphorylation participates in the trafficking of secretory granules (SGs), synaptic vesicles (SVs), and synaptic-like microvesicles (SLMVs) of neuroendocrine cells, including pancreatic β-cells. Several membrane and cytosolic phosphoproteins involved in priming, docking and fusion of regulated secretory vesicles (Ferro-Novick, S. et al., Nature 370:191–193 (1994); Martin, T. F., Curr. Opin. Neurobiol. 4:626–632 (1994); Calakos, N. et al., Physiol. Rev. 76:1–29 (1996)) have been shown to be substrates for serine/threonine phosphorylation (Greengard, P. et al., Science 259:780–785 (1993); Ashcroft, F. M. et al., J. Cell Biochem. 55 Supp:54–65 (1994)). However, less evidence is available implicating tyrosine phosphorylation in these processes. The following evidence suggests that tyrosine phosphorylation may play a role in regulated secretion.

The protein tyrosine kinase (PTK) inhibitors genistein and herbimycin A both stimulate insulin secretion in neonatal islets (Sorenson, R. L. et al., Endocrinol. 134:1975–1978 (1994)), and genistein has been shown to affect the ATP-dependent priming of SGs in semi-intact PC12 cells (Hay, J. C. et al., J. Cell Biol. 119:139–151 (1992)). In GH3 cells, both PTK and protein tyrosine phosphatase (PTP) inhibitors have been shown to impair the biogenesis of SGs from the trans-Golgi network (Austin, C. D. et al., J. Cell Biol. 135:1471–1483 (1996)) as well as modulate the activity of L-type $Ca^{2+}$ channels (Cataldi, M. et al., J. Biol. Chem. 271:9441–9446 (1996)) which are known to be coupled to neurosecretion.

Synaptophysin and synaptogyrin, two intrinsic membrane proteins of SVs, have both been shown to be tyrosine phosphorylated (Pang, D. T. et al., Proc. Natl. Acad. Sci. U.S.A. 85:762–766 (1988); Stenius, K., et al., J. Cell Biol. 131:1801–1809 (1995)), but the physiological relevance has not yet been determined. Furthermore, PTK $pp60^{c-src}$ has been shown to be peripherally associated with regulated secretory vesicles, including SGs of chromaffin cells (Parsons, S. J. et al., Biochem. Biophys. Res. Comm. 134:736–742 (1986); Grandori, C. et al., J. Cell Biol. 107:2125–2135 (1988)).

Annexins (soluble $Ca^{2+}$ and phospholipid-binding proteins) have been implicated in exocytosis in different cell types, including endocrine cells (Burgoyne, R. D. et al., J. Anat. 183:309–314 (1993)). Annexin II, in particular, has been shown to bind chromaffin SGs and to reconstitute secretion from permeabilized chromaffin cells of the adrenal medulla (Sarafian, T. et al., C.J. Cell Biol. 114:1135–1147 (1991)), and has been shown to be tyrosine phosphorylated by $60^{c-src}$ (Hubaishy, I. et al., Biochemistry 34:14527–14534 (1995)). $pp60^{c-src}$ has also been shown to phosphorylate botulinum A and E (Ferrer-Montiel, A. V. et al., J. Biol. Chem. 271:18322–18325 (1996)), two clostridium neurotoxins which cause the block of neurosecretion and paralysis by cleaving the synaptobrevin binding protein SNAP-25 at neuromuscular junctions (Tonello, F. et al., Adv. Exp. Med. Biol. 389:251–260 (1996)). Since tyrosine phosphorylation enhances the protease activity of both botulinum A and E, it is possible that tyrosine phosphorylation and regulated secretion are coupled in certain cells.

Islet cell autoantigen 512 (ICA512, also known as IA-2 and PTP35), is an intrinsic membrane protein of SGs which is expressed in virtually all neuroendocrine cells including peptide-secreting endocrine cells, neurons of the autonomic nervous system, and neurons of the hypothalamus and the amygdala in the brain (Solimena, M. et al., EMBO J. 15:2102–2114 (1996)). Human ICA512 has been identified as an autoantigen of IDDM (Rabin, D. U. et al., Diabetes 41:183–186 (1992); Rabin, D. U. et al., J. Immunol. 152:3183–3188 (1994); Lan, M. S. et al., DNA Cell Biol. 13:505–514 (1994)), and has been postulated to play a role in regulated peptidergic secretion from neuroendocrine cells, including insulin-secreting cells of the pancreatic islets. The open reading frame of human ICA512 encodes a protein of 979 amino acids (FIG. 1). The sequence includes a signal peptide (residues 1–34) and two putative N-glycosylation sites (residues 506 and 524) in the extracellular domain (residues 1–575, henceforth defined as ectodomain), a single transmembrane domain (residues 576–600), and a cytoplasmic domain (residues 601–979) which includes a region displaying homology to protein tyrosine phosphatases (PTPs) (residues 696–979). Like several other enzymatically active receptor protein tyrosine phosphatases (RPTPs) (Streuli, M. et al., EMBO J. 11:897–907 (1992); Serra-Pages, C. et al., J. Biol. Chem. 269:23632–23641 (1994); Brady-Kalnay, S. M. et al., J. Biol. Chem. 269:28472–28477 (1994); Pulido, R. et al, Proc. Natl. Acad. Sci. U.S.A. 92:11686–11690 (1995)), ICA512 is processed within its ectodomain (Solimena, M. et al., EMBO J. 15:2102–2014 (1996); Hermel et al., Eur. J. Neurosci. 11:20690 (1999)). Cleavage of ICA512 (arrow in FIG. 1) generates a 65 kD transmembrane fragment (residues 449–979) which remains associated with SG membranes, and a putative N-terminal fragment (residues 35–448).

The cytoplasmic domain of ICA512 is homologous with PTPs and suggests that ICA512 participates in signal transduction pathways involving tyrosine phosphorylation. Several features, however, distinguish ICA512 from conventional RPTPs.

First, the ectodomain of human ICA512 does not contain any of the motifs found in most RPTPs, including Ig domains, type III fibronectin repeats, MAM (meprin, A5, PTPμ) domains, or carbonic anhydrase-like motifs, all of which are thought to mediate cell—cell or cell-matrix contact (Brady-Kalnay, S. M. et al., Curr. Opin. Cell Biol. 7:650–657 (1995); Streuli, M. Curr. Opin. Cell Bio. 8:182–188 (1996)). (The RGD motif of the type III fibronectin repeat, however, is present once in the ectodomains of rat and mouse ICA512 (Passini, N. et al., Proc. Natl. Acad. Sci. U.S.A. 92:9412–9416 (1995); Lu, J. et al., Biochem. Biophys. Res. Comm. 204:930–936)).

Second, ICA512 joins phogrin and striate enriched phosphatase (STEP) isoforms as a member of the RPTP family which resides in an intracellular compartment (Rydelk, F. L. et al. Soc. Neurosci. 22:1005 (400.5) (1996); Bult A., et al., J. Neuroscience 16:7821–7831 (1996)). In contrast, the majority of other receptor protein tyrosine phosphatases are believed to be constitutively expressed at the plasma membrane. Phogrin (also known as IA-2β or ICAAR), in particular, is a mammalian protein with significant structural and most likely functional homology to ICA512 (Wasmeier, C. et al., J. Biol. Chem. 271:18161–18170 (1996)). Phogrin is also associated with secretory granules of neuroendocrine cells, including β-cells, and is an autoantigen of IDDM (Pietropaolo, M. et al., Diabetes Care 20:208–214 (1997); Hatfield, E. C., Diabetologia 40:1327–1333 (1997)).

Third, recombinant ICA512 does not display PTP activity when tested with common PTP substrates (Rabin, D. U. et al., Diabetes 41:183–186 (1992); Lan, M. S. et al., DNA Cell Biol. 13:505–514 (1994); Lu, J. et al., Biochem. Biophys. Res. Com. 204:930–936 (1994)). The lack of catalytic activity of ICA512 results from two amino acid substitutions within its PTP homology domain: an aspartic acid (D) instead of an alanine (A) at position 911 within the so-called PTP "signature motif", and an alanine instead of an aspartic acid at position 877. However, an ICA512 mutant in which alanine 877 and aspartic acid 911 have been replaced with aspartic acid and alanine, respectively, displays PTP activity similar to conventional PTPs (Magistrelli, G. et al., Biochem. Biophys. Res. Comm. 227:581–588 (1996)). In addition, replacement of aspartic acid with alanine within the PTP signature motif of phogrin is sufficient to confer PTP activity (Rydelk, F. L. et al. Soc. Neurosci. 22:1005 (400.5) (1996)).

There is evidence that other members of the RPTP family interact with proteins of the spectrin family. CD45, a receptor involved in T- and B-cells proliferation, has been shown to bind βII-spectrin (also known as β-fodrin) via its C-terminus PTP domain (Iida et al., J. Biol. Chem. 269:28576–28583 (1994)). Striikingly, this PTP domain in CD45, like that in ICA512, contains an aspartic acid rather than an alanine within its PTP signature motif and appears to be enzymatically inactive. A protein termed TRIO, which contains multiple spectrin repeats, has been recently found to interact with the regulatory, enzymatically inactive, PTP domain of RPTP LAR (Debant, A. et al., Proc. Natl. Acad. Sci. U.S.A. 93:5466–5471 (1996)). Taken together, this data suggests that modified, non-catalytic PTP domains may mediate the interaction of RPTPs with the actin cytoskeleton via an interaction with different members of the spectrin family.

There is also evidence that spectrins can be the targets of autoimmunity in human diseases. For instance αII-spectrin (also known as α-fodrin) has been recently found to be a major autoantigen in Sjorgren syndrome (Haneji, N. et al., Science 276:604–607 (1997); Yanagi et al., Eur. J. Immunol. 28:3336 (1998)), a disorder resulting from the autoimmune infiltration of the salivary gland. Recently, both cellular and humoral autoimmunity directed against αII-spectrin has been detected in the non-obese diabetic (NOD) mouse (Yanagi et al., Eur. J. Immunol. 28:3336–3345 (1998)), a mouse strain that spontaneously develops an autoimmune sialadenitis resembling human Sjogren syndrome as well as an autoimmune diabetes resembling human type I diabetes. These data raise the question of whether autoimmunity directed against αII-spectrin can develop in type I diabetic patients in the absence of Sjogren syndrome. Relevant to this question is whether αII-spectrin is expressed in pancreatic β-cells. To the inventor's knowledge, no members of the spectrin family, including αII-spectrin, has been reported to be expressed in pancreatic β-cells.

Heretofore, studies on vesicular trafficking in neuroendocrine cells and signal transduction via tyrosine phosphorylation have proceeded without significant overlap. Recently, however, it has been postulated that a close relationship may exist between the cell biology of regulated secretion and the organization of the cortical cytomatrix, a preferential target for tyrosine phosphorylation. ICA512 and phogrin could each play a role in regulating peptide hormone secretion and/or survival and differentiation of neuroendocrine cells. However, the precise role of these autoantigens remains elusive, as the proteins appear to lack PTP activity. Therefore, there is a need in the diabetes treatment art for the identification, isolation, and characterization of protein molecules, or fragments thereof, that associate with autoantigens of type I diabetes, such as human ICA512 and phogrin, in order to assist in the determination of the precise role of these autoantigens in peptide hormone secretion. In addition, such proteins, or fragments thereof, could be the targets of autoimmunity in human diseases related to peptide hormone secretion, including IDDM, and hence would be useful as a tool in attenuating or screening for such diseases. The present invention is believed to be an answer to that need.

SUMMARY OF THE INVENTION

In one aspect, the present invention relates to an isolated polypeptide (termed βIV-spectrin), or a fragment thereof, the isolated polypeptide, or fragment thereof, having an amino acid sequence shown in SEQ ID NO:2 (FIG. 3), or a fragment thereof.

In another aspect, the present invention relates to an isolated nucleic acid which codes for a polypeptide, or fragment thereof, wherein the polypeptide or fragment thereof has the amino acid sequence shown in SEQ ID NO:2 (FIG. 3), or a fragment thereof.

In another aspect, the present invention relates to a method for identifying the presence of type I diabetes in a patient, comprising the steps of (a) contacting body fluid from the patient with an isolated polypeptide, or fragment thereof, which interacts with an autoantibody of type I diabetes to form a complex, the isolated polypeptide or fragment thereof comprising the amino acid sequence shown in SEQ ID NO:2 (FIG. 3), or a fragment thereof; and (b) detecting the presence or absence of the complex.

In yet another aspect, the present invention relates to a method of modulating neuropeptide or hormone release in a patient, comprising the step of administering to a patient a therapeutic amount of a compound which affects the interaction of an autoantigen of type I diabetes and a polypeptide which interacts with the autoantigen of type I diabetes, the polypeptide having the an amino acid shown in SEQ ID NO:2 (FIG. 3), or a fragment thereof. Preferably, the compound binds to the product of a gene that encodes a polypeptide having an amino acid sequence comprising at least one sequence of Glu-Arg-Gln-Glu-Ser (SEQ ID NO:3).

In yet another aspect, the present invention relates to a pharmaceutical composition comprising a therapeutic amount of a compound which affects the interaction of an autoantigen of type I diabetes and a polypeptide which interacts with the autoantigen of type I diabetes in a pharmaceutically acceptable carrier, the polypeptide having the amino acid sequence shown in SEQ ID NO:2 (FIG. 3) or a fragment thereof, the pharmaceutical composition effective to modulate neuropeptide or hormone release in a patient. Preferably, the compound binds to the product of a gene that encodes a polypeptide having an amino acid sequence comprising at least one sequence of Glu-Arg-Gln-Glu-Ser (SEQ ID NO:3).

These and other aspects will become apparent upon reading the following detailed description of the invention.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The invention will be more fully understood from the following detailed description taken in conjunction with the accompanying drawings in which:

FIG. 5 shows the partial cDNA (SEQ ID NO:1) and deduced polypeptide (SEQ ID NO:2) sequences for human IV-spectrin;

DETAILED DESCRIPTION OF THE INVENTION

Figure 1:
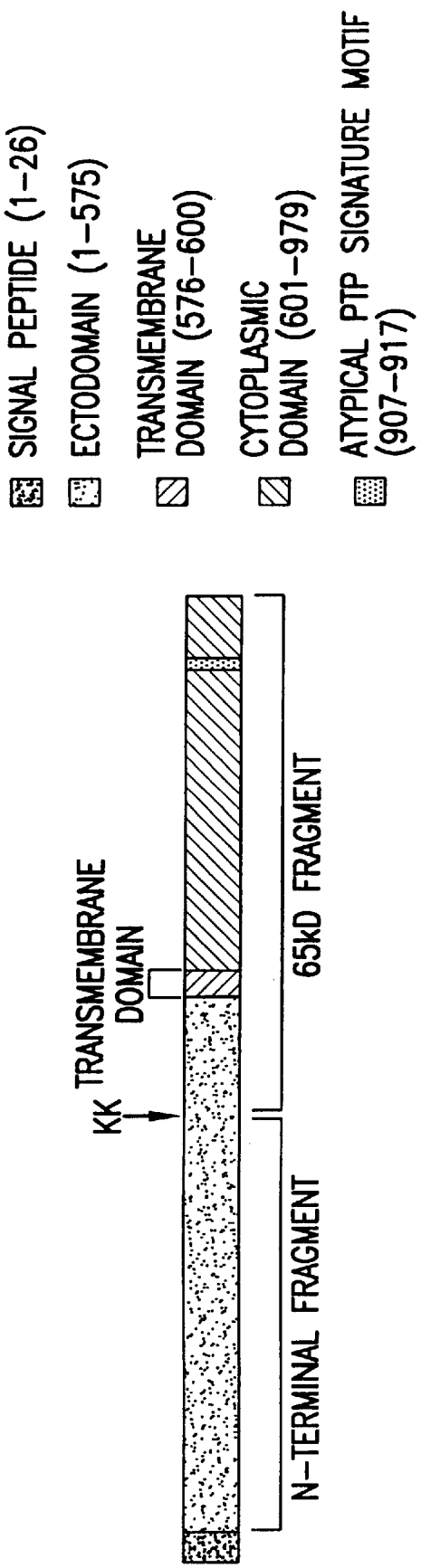
FIG. 1 is a schematic diagram of the domain structure of human ICA512.

It now has been surprisingly found, in accordance with the present invention, that an answer is provided to the problem of identifying, isolating, and characterizing a protein or protein fragment that associates with autoantigens of type I diabetes, particularly ICA512 and phogrin. The present inventors have solved this problem by isolating, identifying, and partially cloning a novel human protein termed βIV spectrin, a new member of the spectrin family, which selectively associates with the cytoplasmic domain of human ICA512 ($ICA512_{cyt}$) and phogrin. As an interactor of ICA512 and phogrin, βIV-spectrin is a potential target of autoimmune diseases, such as type I diabetes, and is useful in screening sera and body fluids from individuals affected by type I diabetes or at risk of developing this disease. In addition, βIV-spectrin is a potential target for pharmacological intervention in disorders such as diabetes which result from impaired hormone secretion.

Since βIV-spectrin is a new member of the spectrin family as described in detail hereinbelow, the present inventor postulates that other members of the spectrin family (i.e., those proteins with spectrin or spectrin-like repeats in their amino acid sequences), such as alpha and beta isoforms of erythroid spectrin and non-erythroid spectrin (β-fodrin), may also associate with autoantigens of type I diabetes and thus represents additional targets of autoimmunity in such disease. Accordingly, the methods and compositions of the present invention are not limited to βIV-spectrin, but includes all members of the spectrin family that associate with autoantigens of type I diabetes.

As used herein, the term "interacts" is defined as any mutual or reciprocal interaction between molecules, particularly the binding between two or more molecules.

As defined herein, the term "autoantigen" refers to a molecule created by an organism, such as a human, for which there is an immune response by that organism, for example, generation of ICA512 or phogrin.

As defined herein, the phrase "spectrin repeat" or "spectrin-like repeat" refers to one or more sequences of amino acids that are characteristic of those proteins which are members of the spectrin family.

The original cDNA clone encoding a portion of the βIV spectrin gene was isolated following a screening for human brain proteins interacting with the cytoplasmic domain of ICA512 by two hybrid assay in yeast. The two-hybrid system in *S. cerevisiae* is an assay in which protein-protein interactions are identified in vitro through the reconstitution of the activity of a transcriptional activator (Fields, S. et al., Nature 340:245–246 (1989)). In general, this system is well suited for the identification of interactions that occur in the cytosol or the nucleus. The conventional two-hybrid system is based on the modular structure of eukaryotic transcription activators, many of which contain two distinct domains: one which binds DNA and other which activates transcription. To promote transcription, the DNA-binding and activation domains must be adjacent, but not covalently attached. In this method, the cDNA encoding for a DNA-binding domain is fused to the cDNA of a protein ("bait") for which interactors are to be found, whereas the cDNA for a transcription activation domain is fused to proteins ("preys") encoded by a cDNA library. The bait and prey fusion genes reside on independent plasmids which are co-transformed into a yeast strain whose growth in media lacking an essential amino acid (such as histidine) depends on the expression of the corresponding biosynthetic enzyme. This occurs only when the association of the two fusion proteins brings the DNA-binding and transcription activation domains into close proximity. In a similar fashion, the interaction of the bait and prey induces the expression of β-galactosidase encoded by the LacZ gene.

For the present invention, the yeast two-hybrid screening was executed according to the protocol of Vojtek (Vojtek et al., 1993). Briefly, the cDNAs encoding for the cytoplasmic domains of the wild-type human ICA512 (a.a.600–979, ICA512-cyt), human phogrin (a.a. 640–1015, phogrin-cyt) and the ICA512 A877D911/D877A911 (ICA512-cyt AD/DA) mutant were amplified by polymerase chain reaction (PCR) and independently subcloned into the pLexA vector, creating fusion proteins with the LexA binding domain. The ICA512 AD/DA mutant was constructed using site directed mutagenesis of human ICA512 in pRC/RSV (Invitrogen, Carlsbad, Calif.) with the QuickChange mutagenesis kit (Stratagene, La Jolla, Calif.) according to the manufacturer's instructions (A877/D877, 5' primer: CCTCAGCTGGCCGGACGAGGGCACACCGG (SEQ ID NO:4), 3' primer: CCGGTGTGCCCTCGTCCGGC-CAGCTGAGG (SEQ ID NO:5); D911'A911, 5' primer: CGTGCACTGCTCGGCCGGTGCGGGGAG (SEQ ID NO:6); 3' primer: CTCCCCGCACCGGCCGAGCAGTG-CAC (SEQ ID NO:7). Insertion of point mutations was verified by restriction analysis and automated sequencing. The cytoplasmic domain of human phogrin was amplified by PCR from a human adult brain cDNA library in pACT2 (Clontech, Palo Alto, Calif.) and analyzed by automated sequencing. pLexA-ICA512-cyt, pLexA-ICA512-cyt AD/DA and pLexA-phogrin cyt were independently transformed into the yeast strain L40 (partial genotype MATa trp1 leu2 his3 LYS2::lexA-HIS3 URA3::lexA-lacZ) and AMR70. Expression of the LexA-fusion proteins (baits) was verified by western blotting using a pLexA-antibody (Invitrogen, Carlsbad, Calif.). L40 cells expressing pLexA-ICA512cyt were co-transformed with 500 µg human adult brain MatchMaker cDNA library in PACT2 (Clontech). Double transformants were selected and screened for His+ and LacZ+ phenotype, demonstrating the presence of a functional ligand for ICA512cyt. Screening of 1×107 double transformants yielded about 800 His+ colonies, of which about 540 were LacZ+. A subset of these clones was screened a second time by a mating assay. Briefly, after the purging of the bait plasmid (pLexA-ICA512cyt), the L40 His+ LacZ+ cells carrying the prey plasmids were mated with AMR70 cells transformed either with LexA-ICA512cyt, LexA-ICA512cyt, AD/DA or LexA-phogrin cyt. Mating with LexA-lamin and LexA-mss4, two mammalian proteins unrelated to ICA512 and phogrin, allowed segregation of false positive clones from putative ICA512 interactors. One of the clones that fulfilled the requirements for specificity of the mating assay was sequenced completely on both strands. This clone, termed B8, contained an insert of 2,420 base pair located at the 3' end of a novel gene with sequence similarity to members of the spectrin family.

Figure 2A:
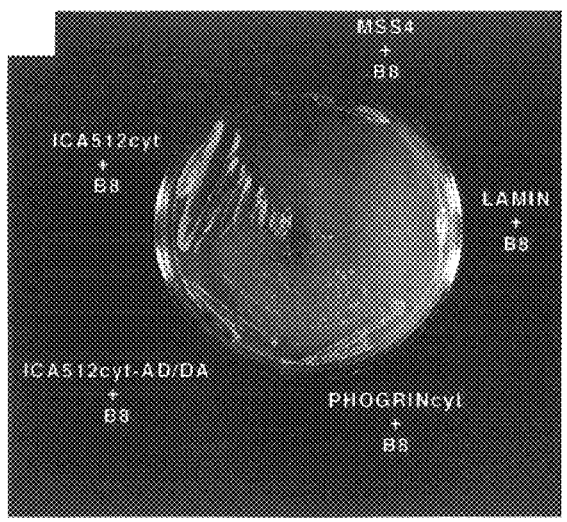
FIGS. 2A–B are photographs showing the results of a two-hybrid screening in yeast for ICA512 and phogrin binding proteins and C–D are western blot analyses for the expression of ICA512 cytoplasmic domain, phogrin cytoplasmic domain, and a polypeptide encoded by the IV-spectrin gene (hereafter termed B8)
Figure 2B:
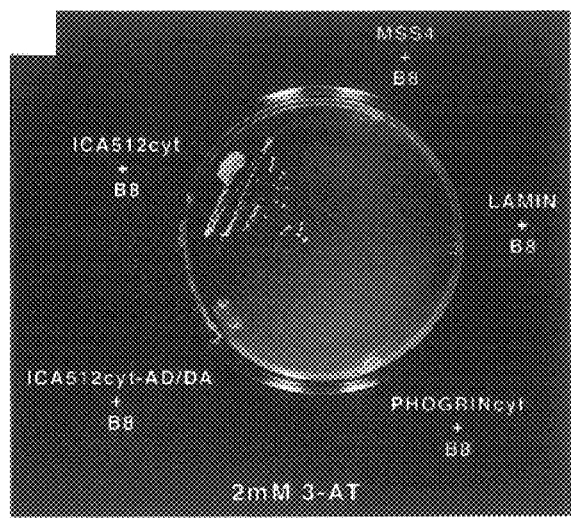

Panel A of FIG. 2 shows results of the two-hybrid system analysis in the absence of 3-aminotetrazole (3-AT), an inhibitor of the HIS3 reporter gene necessary for histidine synthesis. With reference to panel A of FIG. 2, diploid cells expressing the cytoplasmic tail of human ICA512 (ICA512-cyt) fused to the DNA binding protein LexA and the B8 polypeptide fused to the GAL4 activation domain survive in the absence of histidine in the media. This result suggests that the B8 olypeptide interacts with ICA512-cyt and leads to the transcription of the reporter gene HIS3.

On the contrary, the unrelated control baits lamin and MSS4 (panel A of FIG. 2) do not interact with the B8 polypeptide, suggesting that the B8 polypeptide does not interact with all proteins. In addition to wild type ICA512-cyt, B8 binds to the cytoplasmic tail of phogrin (phogrin-cyt), a portion of phogrin which is 74% identical to the corresponding region of ICA512. Further, B8 interacts with ICA512-cyt AD/DA, a mutant wherein alanine-877 and aspartic acid-911 of the atypical PTP-like domain of the protein are replaced with aspartic acid and alanine, respectively, both of which are present in conventional PTPs.

Panel B of FIG. 2 shows results of the two-hybrid mating assay performed in more stringent conditions due to the presence of 2 mM 3-AT. As shown in FIG. 2, panel B, under these conditions, ICA512-cyt AD/DA and phogrin-cyt do not appear to bind B8, whereas an interaction still occurs in cells expressing wild type ICA512-cyt and B8 polypeptide. These data suggest that the B8 polypeptide interacts more strongly with ICA512-cyt than with ICA512-cyt AD/DA or phogrin-cyt, and that the atypical PTP domain of ICA512 is involved in this association.

FIG. 2, panel C, shows a Western blot for ICA512-cyt (lane 1), ICA512-cyt AD/DA (lane 2), and phogrin-cyt (lane 3), each expressed in combination with B8 as described above and probed with anti-LexA antibodies. As shown in panel C, in diploid yeast cells, ICA512-cyt is expressed significantly less than ICA512-cyt AD/DA and phogrin-cyt. Panel D of FIG. 2 shows a Western blot for B8 in the same diploid yeast cells using an anti-HA antibody. This Western blot show that all diploid cells express similar amounts of B8. The results of these experiments rule out the possibility that survival of diploid yeast cells expressing ICA512-cyt and B8 in the presence of 2 mM 3-AT (FIG. 4B) is due to a higher level of expression of ICA512-cyt compared with ICA512-cyt AD/DA or phogrin-cyt and is consistent with the notion that B8 binds ICA512-cyt with higher affinity than ICA512-cyt AD/DA and phogrin-cyt.

Figure 3:
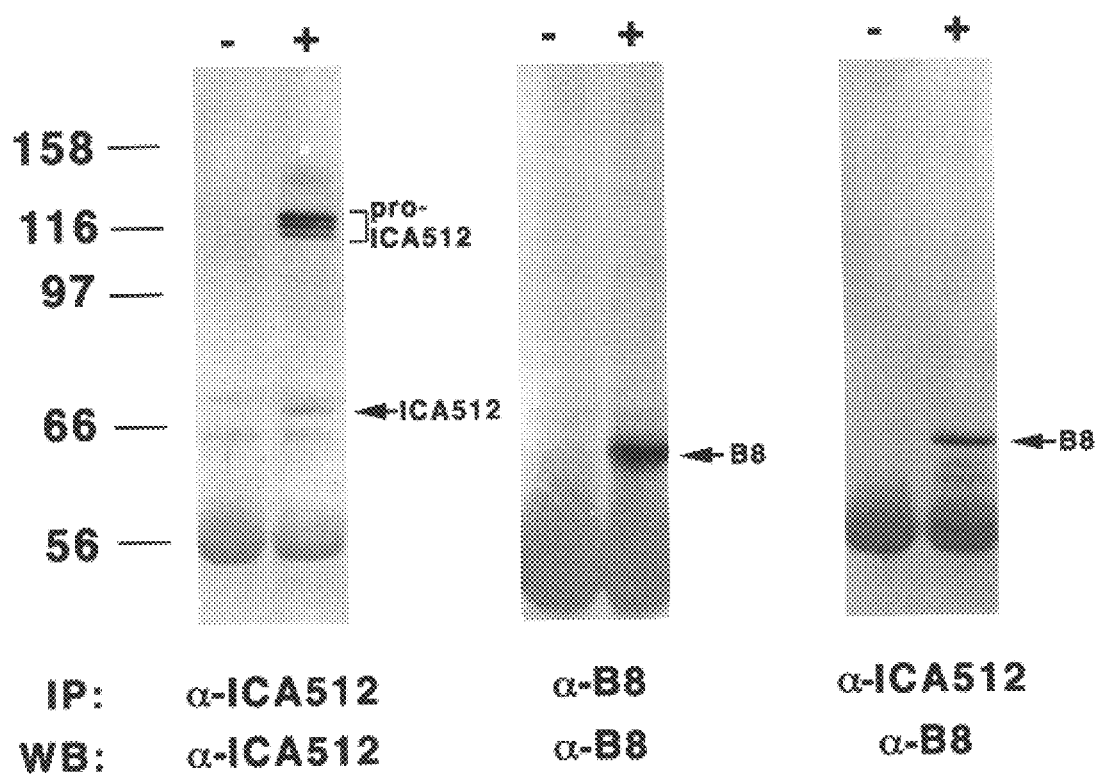
FIG. 3 is a photograph of an immunoprecipitation and western blot analysis of the fragment of IV-spectrin B8 interacting with ICA512 protein.

The interaction of B8 with ICA512 was been confirmed biochemically by co-immunoprecipitation experiments in combination with Western blot (FIG. 3). Briefly, the cDNAs of human ICA512 and the B8 clone were subcloned into the pRC/RSV expression vector (Invitrogen, Carlsbad, Calif.). A starting methionine and a Kozak's sequence at the 5'-end of the B8 cDNA were introduced by standard procedures using the PCR. Transient co-transfection of cultured COS cells (Gluzman, 1981) was carried out with the $Ca^{2+}$-phosphate procedure (Chen et al., 1987; Hanson et al., 1989) by using a mixture containing 15 µg of each plasmid.

Seventy-two hours after transfection, COS cells were solubilized with 1 ml of homogenization buffer (HB) containing 2% Triton X-100 for 90 min. One confluent 10 cm dish of transfected cells was used for each immunoprecipitation. 2% Triton X-100 insoluble material was removed from the extracts by centrifugation at 15,000 g× for 30 min. After pre-clearance of the Triton X-100 soluble material with protein G-sepharose beads (50% w/vol; Pharmacia, Piscataway, N.J.) for 1 hr, 10 μl of α-ICA512 monoclonal antibody or 10 μl of the rabbit antiserum directed against βIV-spectrin were added to 1 ml Triton-X-100 extract and incubated overnight on a rocking platform at 40° C. Following the addition of 50 μl protein G-sepharose beads for 1 hr the immunocomplexes were recovered by centrifugation at 16,000×g, washed, and separated on 8% SDS-PAGE. Separated proteins were transferred onto nitrocelluose and immunoblotted with rabbit anti-ICA512 (1:1000) or anti-βIV-spectrin antibodies (1:1000) followed by goat anti-rabbit antibodies conjugated to alkaline phosphatase (1:5,000; Sigma, S. Louis, Ind.).

In the above assay, antibodies for use in the immunoblots were prepared as follows. A 21-mer synthetic peptide (CEELPRRRRPERQESVDQSEE, SEQ ID NO:8) including residues 1970–1989 of βIV-spectrin was coupled to bovine thyroglobulin and injected into rabbits to generate a polyclonal antiserum. The serum of one immunized rabbit recognized the recombinant polypeptide encoded by the B8 cDNA expressed in *E. coli* by western blotting. Anti-βIV-spectrin antibodies from this serum were affinity purified on the immunogenic peptide that had been covalently coupled to agarose beads using an AminoLink kit (Pierce, Rockford, Ill.). Anti-βIV-spectrin antibodies were eluted from the column with 0.1 N acetic acid, pH 2.5 and immediately brought back to neutral pH with 1M Tris, pH 9.0.

As shown in FIG. 3, pro-ICA512 appears as a triplet of ~115 kD (bracket), whereas mature ICA512 has a molecular weight of ~70 kD (arrow in the left panel). Two arrows in the center and right panels point to immunoprecipitated B8 at the expected molecular weight of ~60 kD. Detection of B8 in the immunoprecipitates from co-transfected COS cells, but not from wild-type COS cells, indicates that this protein was immunoprecipitated specifically together with ICA512 by the anti-ICA512 monoclonal antibody. Likewise, ICA512 co-immunoprecipitated with B8 after incubation of detergent extracts from co-trasfected COS cells with anti-B8 antibodies (data not shown).

Having established that the B8 polypeptide interacts with the cytoplasmic domain of ICA512 by two independent assays (two-hybrid screening in yeast and co-immunoprecipitation experiments from transfected fibroblasts), the remaining 5' end portion of the gene encoding the B8 polypeptide, i.e. the bIV-spectrin cDNA, was cloned.

To clone the 5'-end of the βIV-spectrin cDNA, a 300 base pair fragment contained within the B8 cDNA clone was amplified by PCR and labeled with [α-$^{32}$p-dCTP] (3,000 Ci/mmol, Amersham, Arlington Heights, Ill.) using the Random Prime Labeling Kit (Amersham). This probe was used to screen 2×10$^6$ independent phages from a λgt-11 human brain cDNA library (Clontech, Palo Alto, Calif.). Three independent positive phages were isolated whose cDNA insert partially overlapped with the original cDNA B8 clone isolated by two-hybrid. Screenings of a λgt-10 human brain cerebellum library (Clontech, Palo Alto, Calif.) resulted in the isolation of additional 20 independent phages. Sequencing of the cDNA inserts from the isolated phages allowed the assembly of the 7,812 base pair cDNA of βIV-spectrin shown in SEQ ID NO:1 (FIG. 5), discussed below. Automated sequencing was performed by the Keck Biotechnology Resource Laboratory at Yale University School of Medicine. DNA computer assisted analysis was executed using BLAST (Altschul et al., 1990) and SWISS-PROT (University of Geneva, Switzerland) and Lasergene software (DNASTAR Inc, Madison, Wis.).

Figure 4:
FIG. 4 is a schematic diagram of the partial domain structure of human IV-spectrin polypeptide.

The most significant features of the βIV-spectrin molecule are shown generally in FIG. 4. As shown in FIG. 4, the partial primary sequence of the βIV-spectrin molecule includes multiple (17) spectrin-like repeats, region designated as βIV U including a unique tetrarepeat of specific amino acids, a proline-rich domain (designated as PRD), and a pleckstrin homology domain (designated as PH). These features of the primary sequence of βIV-spectrin are discussed in more detail below.

Figures 1, 5F:
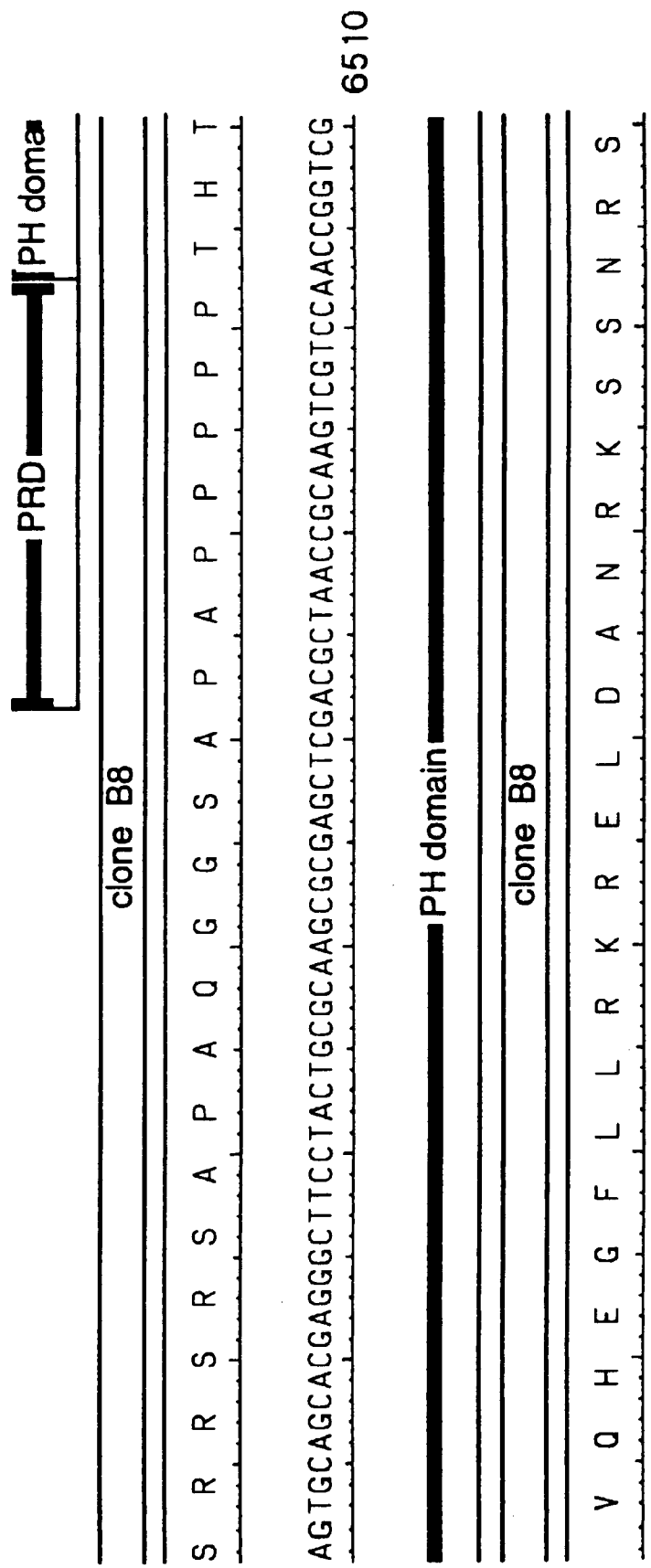

FIG. 5 shows in more detail the partial cDNA sequence (SEQ ID NO:1) and corresponding translated protein sequence (SEQ ID NO:2) of human βIV-spectrin. As shown in FIG. 5 and in SEQ ID NOS: 1 and 2, this cDNA sequence is 7,812 nucleotides in length and codes for a protein of about 2,293 amino acids having a predicted MW of approximately 252 kD. An open reading frame ranges from nucleotides 1–6,879. The primary sequence of the βIV-spectrin protein includes several significant structural features as shown in Table 1.

TABLE 1

| Structural Features of the βIV-Spectrin Polypeptide | |
| --- | --- |
| Feature | Location |
| Putative actin binding domain (partial) | residues 1–12 |
| Spectrin repeat 1 | residues 13–282 |
| Spectrin repeat 2 | residues 283–624 |
| Spectrin repeat 3 | residues 625–936 |
| Spectrin repeat 4 | residues 937–1323 |
| Spectrin repeat 5 | residues 1324–1638 |
| Spectrin repeat 6 | residues 1639–1965 |
| Spectrin repeat 7 | residues 1966–2217 |
| Spectrin repeat 8 | residues 2218–2595 |
| Spectrin repeat 9 | residues 2596–2919 |
| Spectrin repeat 10 | residues 2920–3234 |
| Spectrin repeat 11 | residues 3235–3573 |
| Spectrin repeat 12 | residues 3574–3870 |
| Spectrin repeat 13 | residues 3871–4278 |
| Spectrin repeat 14 | residues 4279–4599 |
| Spectrin repeat 15 | residues 4600–4923 |
| Spectrin repeat 16 | residues 4924–5241 |
| Spectrin repeat 17 | residues 5242–5568 |
| Beta IV repeat 1 | residues 5881–5895 |
| Beta IV repeat 2 | residues 5935–5949 |
| Beta IV repeat 3 | residues 5989–6003 |
| Beta IV repeat 4 | residues 6088–6103 |
| Proline–rich domain (PRD) | residues 6412–6432 |
| Pleckstrin homology domain (PH) | residues 6433–6879 |
| Stop Codon | residues 6880–6882 |
| poly adenylation signal (pAS) | residues 7753–7759 |

As indicated in Table 1 above, a partial putative actin binding domain is located from residues 1–12. Seventeen consecutive spectrin repeats are located from residues 13–5568. Four repeating sequences of Glu-Arg-Gln-Glu-Ser (SEQ ID NO:3) unique to βIV-spectrin are positioned at residues 5881–5895, 5935–5949, 5989–6003, and 6088–6103. A proline-rich domain (PRD) is located from residues 6412–6432 of the βIV-spectrin protein sequence. Proline rich domains can mediate the interaction with proteins containing src-homology 3 (SH3) domain (a repeat of approximately 60 amino acids found in many proteins that mediate their assembly with proteins containing proline-rich domains), or WW domains (a domain spanning approximately 35 amino acids which bind to proteins with specific proline-rich motifs and having multiple tryptophan (W) residues).

A pleckstrin homology (PH) domain is located from residues 6433–6879 of the βIV-spectrin primary sequence. Pleckstrin homology domains can bind to proteins or phosphoinositides, and have been shown to mediate the association of proteins with phosphoinositides in membranes as described in Pawson, T. Nature 373:573–580 (1995).

Comparison of βIV-spectrin cDNA and the predicted primary amino acid sequence with publicly available sequences indicates that βIV-spectrin is a new member of the spectrin family. Other members of this family include alpha and beta isoforms of spectrin, some of which are expressed in erythroid cells, while others have a more widespread tissue distribution. βIV-spectrin has been found to be most homologous to the beta chain of non-erythroid spectrin (also known as β-fodrin), which may be involved in neurosecretion.

Figure 6:
FIG. 6 is a photograph showing fluorescent in situ hybridization for βIV-spectrin.

Screening of a human BAC genomic library (Genomic System, S. Loius, Mo.) using a 300 bp probe located within the open reading frame of the gene led to the isolation of a BAC clone (clone F614) containing the human bIV-spectrin gene. The presence of introns and exon boundaries within the bIV-spectrin gene was confirmed by automated sequencing of the isolated BAC clone F614 followed by computer assisted DNA analysis with the Genefinder Software. As shown in FIG. 6, the localization of the human bIV-spectrin gene (in green) was obtained by fluorescence in situ hybridization (FISH) on human chromosomes. Briefly, DNA from clone F614 was labeled with digoxigenin dUTP (Boehringher Mannheim, Indianapolis, Ind.) by nick translation. Labeled probes were combined with sheared human DNA and hybridized to normal metaphase chromosome derived from phytohemagglutinin stimulated peripheral blood lymphocytes from a male donor in a solution containing 50% formamide, 10% dextran sulfate and 2× SSC. Specific hybridization signals were detected by incubating the hybridized slides in fluoresceinated antidigoxigenin antibodies followed by counterstaining with DAPI. The initial experiment resulted in specific labeling of the mid long arm of a group F chromosome. A second set of experiments was conducted in which a genomic clone from the E2A locus (19p13.3) was co-hybridized with clone F614. This experiment resulted in the specific labeling of the short and long arms of chromosome 19. Measurements of 10 specifically hybridized chromosomes 19 demonstrated that F614 is located at a position which is 41% of the distance from the centromere to the telomere of chromosome arm 19q, an area that corresponds to band 19q13.13. A total of 80 metaphase cells were analyzed for each clone with 74 exhibiting specific labeling.

Figure 7:
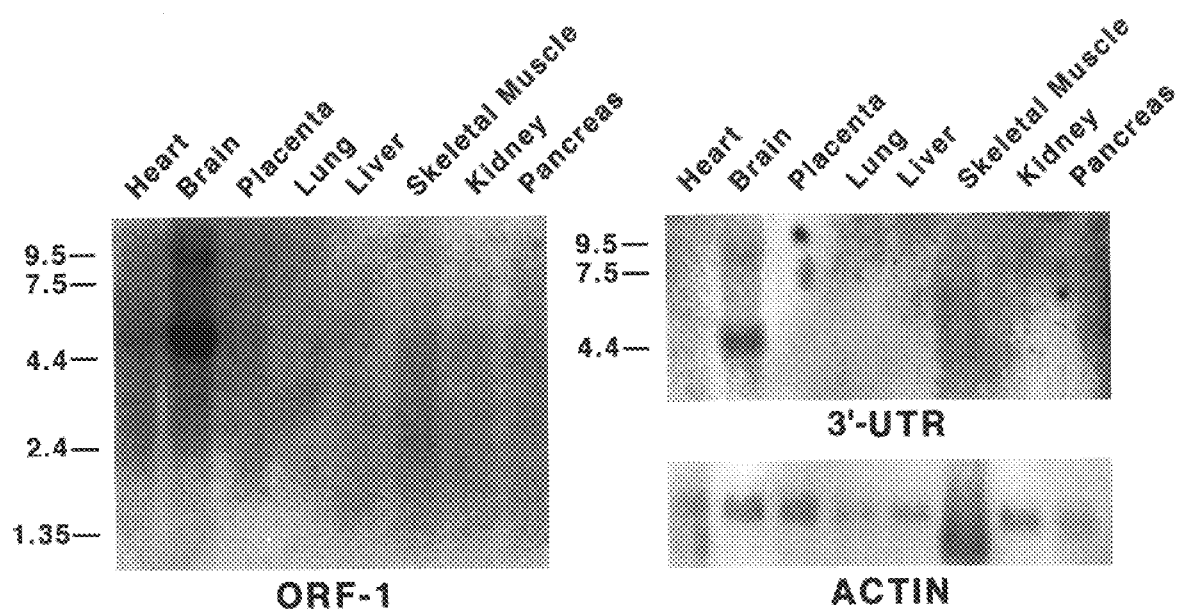
FIG. 7 are autoradiograms showing the results of Northern blot analysis using portions of the βIV-spectrin cDNAs as probes.

To determine the expression of βIV-spectrin in various tissues, a commercial Multi Tissue Northern blot (Clontech, Palo Alto, Calif.) was probed with a ~700 base pair $^{32}$p-labeled cDNA probe located within the open reading frame (ORF-1) of βIV-spectrin according to the manufacturer's instructions. Next, the same blot was stripped and reprobed with a ~700 base pair $^{32}$p-labeled cDNA probe located within the 3'-untranslated region (3'-UTR) of the βIV-spectrin gene. Both probes were obtained by PCR using the B8 cDNA as a template. FIG. 7 shows Northern blot analysis of poly A$^+$ RNA from human tissues with probes in both the open reading frame (ORF-1) and the 3'-untranslated region (UTR) of βIV-spectrin. As shown in FIG. 7, both probes hybridized with two transcripts of ~4.7 kB and 9.5 kB that are predominantly expressed in brain. These data strongly suggest that both transcripts derived from a single gene. Two transcripts of ~4.7 Kb and ~7.5 Kb were detected after long exposure in human heart, skeletal muscle and kidney, while in human pancreas the smaller transcript migrated slightly faster than in the other tissues (data not shown). As a control, the same nitrocellulose filter was probed with an actin probe (FIG. 7).

Figure 8:
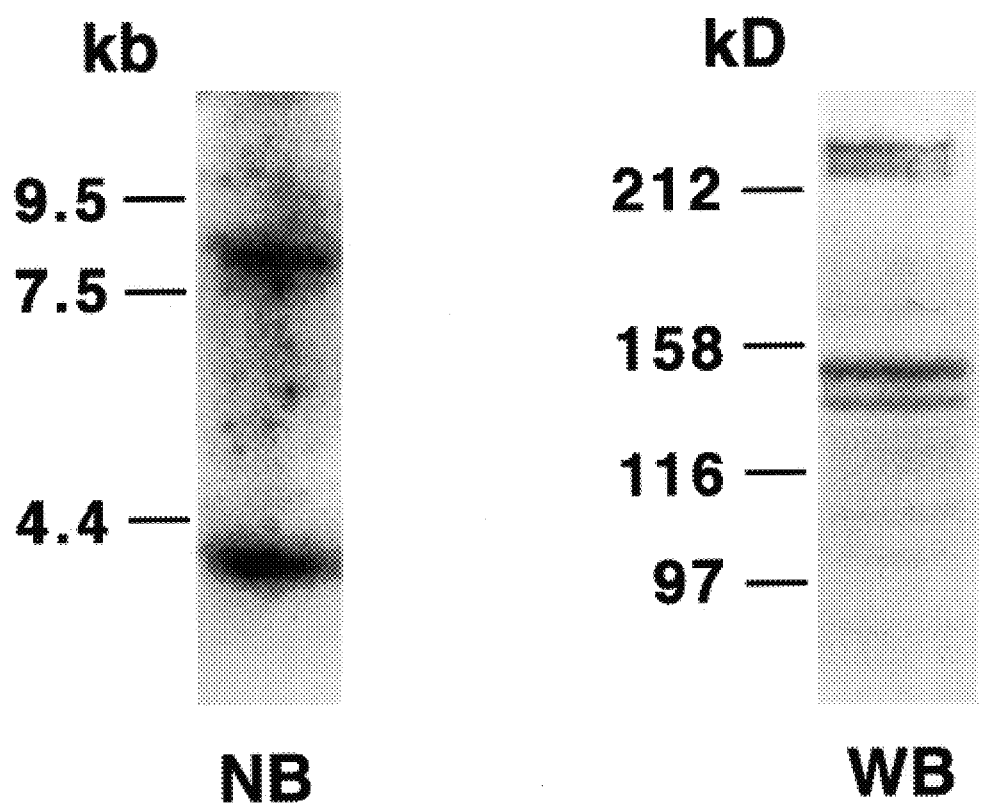
FIG. 8 are autoradiograms of Northern and Western blots for βIV-spectrin in human islets.

Since islets represent ~3% of the total weight of pancreas, islet specific transcripts are significantly under-represented in commercially available RNA preparations. To overcome this limit, a Northern blot was performed on polyA+ RNA isolated from human islets (FIG. 8, NB left panel). Briefly, poly A+ RNA was isolated from 40,000 human islets (kindly provided by the Islet Isolation and Distribution Program at University of Miami, Fla.) using a poly A+ RNA isolation kit (Qiagen, Valencia, Calif.) according to the manufacturer's instructions. 2 μg poly A+RNA was run on a agarose gel containing 2% formaldehyde, blotted overnight on nitrocellulose and probed with the $^{32}$p-labeled ORF-1 probe as described above. As shown in FIG. 8 (NB, left panel), βIV-spectrin mRNA is enriched in human islet cells. Specifically, two major RNA transcripts of 4.2 Kb and 8.3 Kb were detected. The slightly faster migration of these transcripts compared to the transcripts detected in human brain may be accounted by differential tissue-specific alternative splicing of the gene.

Protein expression of βIV-spectrin in human islets was further assesed by Western blot experiments as shown in FIG. 8 (WB, right panel). Approximately 40,000 human pancreatic islets (Human Islet Isolation and Distribution Program, University of Miami, Fla.) were solubilized in 10 mM HEPES, pH 7.4, 150 mM NaCl, 1% Triton X-100, 1 mM phenylmethyl-sulfonylfluoride (PMSF), 10 mM benzamidine, 1 μg/ml aprotinin, 1 μg/ml leupeptin, 1 μg/ml pepstatin A, and 1 μg/ml antipain. Cell extracts were centrifuged for at 100,000×g for 1 hour. Triton X-100 insoluble pellets were resuspended in Laemmli buffer with 2% SDS and separated by 6% SDS-polyacrylamide gel electrophoresis. After transfer onto nitrocellulose, proteins were immunoblotted with affinity purified anti-βIV-spectrin antibodies (1:1000) followed by peroxidase conjugated goat anti rabbit IgG (1:5,000; Sigma, St. Louis, Mo.) and prepared as described above. The signal was detected using the Super-Signal reagents (Pierce, Rockford, Ill.) for enhanced chemiluminescence according to the manufacturer's protocol.

Anti-βIV-spectrin affinity purified antibodies recognize two major protein doublets of ~230 kD and 150 kD (FIG. 8 WB, right panel). These two proteins subsets may represent the products of the two main transcripts detected by Northern blot. The size of the larger species is comparable with that of other beta spectrins, which also migrate at ~230 kD by SDS-PAGE.

Figure 9:
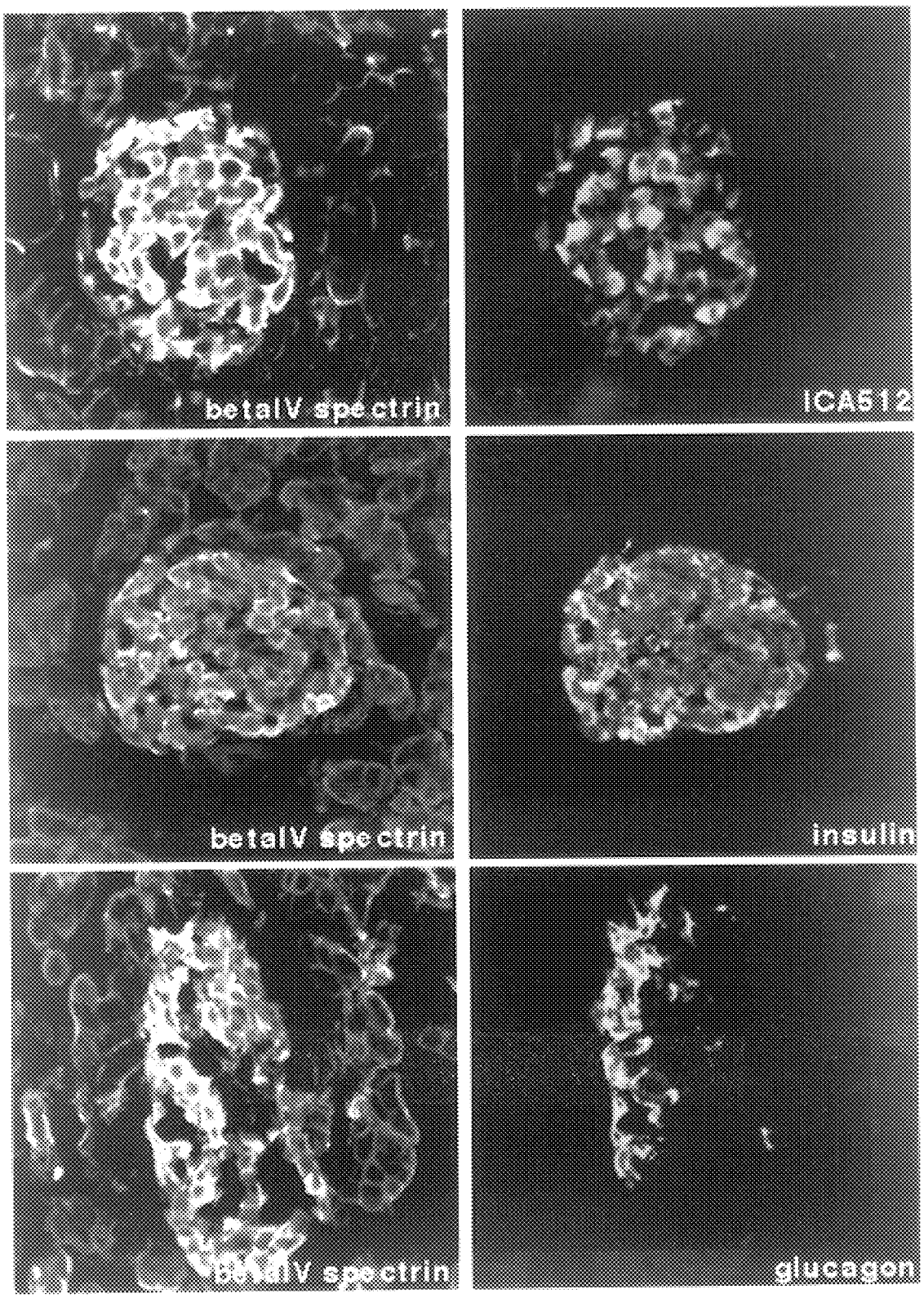
FIG. 9 is a photograph showing the results of stained confocal microscopy on sections of rat pancreas probed with an antibody directed against βIV-spectrin.

FIG. 9 shows confocal microscopy on sections of rat pancreas stained with affinity purified βIV spectrin antibodies. Double immunofluorescence on 12 μm cryostat tissue sections of rat pancreas was performed as described previously (Cameron et al., 1991). Briefly, the tissue sections were incubated for 30 minutes at room temperature in 20 mM phosphate buffer, pH 7.4 containing 16% goat serum, 0.3% Triton X-100 and 0.45 M NaCl (goat serum dilution buffer, GSDB). Next, sections were incubated for 2 hrs with a mixture including either the affinity purified anti-βIV-spectrin antibodies (1:500 dilution) or a rabbit antiserum against αII-spectrin (1:100, Chemicon, Temecula, Calif.) and one of the following mouse monoclonal antibodies: anti-insulin, (1:100, Sigma, St. Louis, Mo.); anti-glucagon (1:100, Sigma, St. Louis, Mo.), or anti-ICA512 (1:200), each prepared as described above. All antibody dilutions were made in GSDB. After multiple washing with phosphate buffer, the sections were incubated in a mixture of goat rabbit (1:100) and goat-anti mouse (1:100) IgG coupled to FITC and Texas red, respectively.

Rat insulinoma INS-1 cells were grown to ~50% confluency on glass-coverslips in DMEM with 10% fetal bovine serum. Before immunostaining, cells were fixed with 4% paraformaldehyde in PBS at room temperature for 30 minutes. Immunolabeling for αII-spectrin and insulin was performed as described above. Confocal microscopy on immunostained tissue sections and cultured cells was performed using a Biorad MRC-1040 system equipped with a krypton—argon laser attached to a Zeiss Axiovert microscope (Zeiss, Thornwood, N.Y.). Acquired images were processed with Adobe Photoshop as described previously (Xu et al., 1992).

The results shown in FIG. 9 demonstrate that βIV-spectrin, similar to ICA512 (top right panel) and phogrin (not shown), is enriched in both α-cells (counterstained for glucagon) and β-cells (counterstained for insulin) of pancreatic islets. Low levels of immunoreactivity are detectable in the surrounding exocrine pancreas.

βIV-spectrin may be suitable for detecting the presence of anti-βIV-spectrin autoantibodies in humans. The methods of the present invention employ purified βIV-spectrin ligand for the anti-βIV-spectrin autoantibodies for detection of such autoantibodies in serum samples. The purified βIV-spectrin ligand will usually be an isolated form, but may also be a βIV-spectrin fragment or other peptide which defines an epitopic binding site capable of specifically binding the anti-βIV-spectrin autoantibodies. It will be appreciated that knowledge of the DNA sequence of the βIV-spectrin gene as well as the amino acid sequence of βIV-spectrin allows identification and preparation of a variety of synthetic peptide compositions which can be utilized as the purified ligand of the present invention. Additionally, the methods of the present invention could utilize anti-idiotypic antibodies capable of specifically binding the anti-βIV-spectrin autoantibodies.

The purified ligand of the present invention may be natural, i.e., intact βIV-spectrin or fragments thereof as described above, isolated from suitable sources. Usually, natural polypeptides will be isolated from CNS cells (e.g., brain tissue) where βIV-spectrin is abundant.

Natural polypeptides may be isolated by conventional techniques such as affinity chromatography. Conveniently, polyclonal or monoclonal antibodies may be raised against previously purified βIV-spectrin and may be utilized to prepare a suitable affinity column by well known techniques. Such techniques are taught, for example, in Hudson and Hay, *Practical Immunology*, Blackwell Scientific Publications, Oxford, United Kingdom, 1980, Chapter 8. Usually, an intact form of βIV-spectrin will be obtained by such isolation techniques. If peptide fragments are desired, they may be obtained by chemical or enzymatic cleavage of the intact molecule.

As an alternative to isolating intact βIV-spectrin from natural sources, it will be possible to prepare synthetic βIV-spectrin proteins and polypeptides based on the sequence of βIV-spectrin which are disclosed herewith. Alternatively, cDNA expression libraries may be screened for a desired form of βIV-spectrin using βIV-spectrin antibodies which are available or may be prepared as described herein.

Synthetic proteins and polypeptides may be produced by either of two general approaches. First, polypeptides having up to about 150 amino acids, usually having fewer than about 100 amino acids, and more usually having fewer than about 75 amino acids, may be synthesized by the well known Merrifield solid-phase synthesis method where amino acids are sequentially added to a growing chain. See, Merrifield, B., J. Am. Chem. Soc. 85:2149–2156 (1963). Apparatus for automatically synthesizing such polypeptides using the solid-phase methodology are now commercially available from numerous suppliers, such as Applied Biosystems, Foster City, Calif.

The second and preferred method for synthesizing the proteins and polypeptides of the present invention involves the expression in cultured mammalian cells of recombinant DNA molecules encoding the desired βIV-spectrin gene portion thereof. The use of mammalian expression system, such as Chinese hamster ovary (CHO) cells, can provide for post-translational modification of the proteins and polypeptides which enhances the immunological similarity of the synthetic products with the native forms of βIV-spectrin. The βIV-spectrin gene may itself be natural or synthetic, with the natural gene obtainable from cDNA or genomic libraries using degenerate probes based on the known amino acid sequence set forth herewith. Alternatively, polynucleotides may be synthesized based on the DNA sequence by well known techniques. For example, single-stranded DNA fragments may be prepared by the phosphoramidite method described by Beaucage and Carruthers in Tetrahedron Lett. 22:1859–1862 (1981). A double-stranded fragment may then be obtained by synthesizing the complementary strand and annealing the strands together under appropriate conditions or by adding the complementary strand using DNA polymerase with an appropriate primer sequence.

The natural or synthetic DNA fragments coding for the βIV-spectrin protein or fragment will then be incorporated in DNA constructs capable of introduction to and expression in an in vitro mammalian cell culture. Usually, the DNA constructs will be capable of replicating in prokaryotic hosts in order to facilitate initial manipulation and multiplication of the construct. After a sufficient quantity of the construct has been obtained, they will be introduced and usually integrated into the genome of cultured mammalian or other eukaryotic cell lines.

DNA constructs suitable for introduction to bacteria or yeast will include a replication system recognized by the host, the βIV-spectrin DNA fragment encoding the desired protein or polypeptide product, transcriptional and translational initiation and regulatory sequences joined to the 5'-end of the structural DNA sequence, and transcriptional and translational termination regulatory sequences joined to the 3'-end of the structural sequence. The transcriptional regulatory sequences will include a heterologous promoter which is recognized by the host.

Conveniently, available cloning vectors which include the replication system and transcriptional and translational regulatory sequences together with an insertion site for the βIV-spectrin DNA sequence may be employed. For transformation of mammalian and other eukaryotic cell lines, co-transfection of the cell lines in the presence of suitable marker, such as DHFR gene, may be employed. Transfection may also be accomplished using chemical or electroporation techniques.

The ligands of the present invention are advantageously utilized in a substantially pure form, that is, typically being at least about 50% w/w (weight/weight) purity, as well as being substantially free from interfering proteins and contaminants. Preferably, the ligands will be isolated or synthesized in a purity of at least about 80% w/w and, more preferably in at least about 95% w/w purity. Using conventional protein purification techniques, homogeneous peptides of at least 99% w/w can be obtained. For example, the proteins may be purified by use of antibodies specific for the βIV-spectrin polypeptide using immunoadsorbent affinity chromatography. Such affinity chromatography is performed by first linking the antibodies to a solid phase support and then contacting the linked antibodies with the source of the ligand polypeptides, e.g., lysates of CNS cells or cells which have been recombinantly modified to produce βIV-spectrin, or of supernatants of cells which have been recombinantly modified to secrete βIV-spectrin when cultured.

For use in purification, antibodies to βIV-spectrin may be obtained by injecting nucleic acids or polypeptides corresponding to βIV-spectrin or βIV-spectrin fragments into a wide variety of vertebrates in accordance with conventional techniques. Suitable vertebrates include mice, rats, sheep, and goats. Usually, the animals are bled periodically with successively bleeds having improved titer and specificity. The antigens may be injected intramuscularly, interperitoneally, subcutaneously, or the like. Usually, vehicles are employed such as a complete or incomplete Freund's adjuvant. Preferably, monoclonal antibodies can be prepared by well-known techniques. In particular, monoclonal FAB fragments may be produced in *E. coli* by the method of Ruse et al. (Science 246:1275–1281 (1989)).

The assays of the present invention will detect the presence of βIV-spectrin in patient sera. It has been found that diabetic and prediabetic patients will usually have autoantibodies to βIV-spectrin. Thus, the preferred assay of the present invention will be able to detect the presence of antibodies reactive with βIV-spectrin. A negative results (i.e., no reaction) will indicate that the patient is neither diabetic nor prediabetic. A positive result will indicate that the patient is diabetic or prediabetic.

Assays according to the present invention typically rely on exposing the purified ligand to a serum sample and detecting specific binding between the ligand and anti-βIV-spectrin autoantibodies which may be present in the serum. Binding between the autoantibodies and purified ligand indicates that the autoantibodies are present, and is diagnostic of a diabetic or prediabetic condition in the patient. Alternatively, such assays can be used to monitor the condition of a patient who has undergone a pancreatic islet cell transplant, where the presence of the anti-βIV-spectrin autoantibodies indicates an adverse immune response to the transplanted cells. The particular assay protocol chosen is not critical, and it is necessary only that the assay be sufficiently sensitive to detect a threshold level of the autoantigen which is considered to be positive.

Assays according to the present invention will be useful for identifying patients who are either prediabetic, i.e., who have circulating autoantibodies to the anti-βIV-spectrin autoantigen but who have not yet suffered sufficient damage to the insulin-producing β-cell to be clinically identified as having IDDM, or who suffer from clinical IDDM. The assays will also be useful for monitoring the effect of immunotherapy to block or prevent autoimmune reactions to the β-cell and for monitoring the progress of the disease from pre-diabetes to clinical diabetes and will be particularly useful for monitoring the status of transplanted pancreatic β-cells in diabetic patients who have undergone an islet cell graft.

Suitable assays include both solid phase (heterogeneous) and non-solid phase (homogeneous) protocols. The assay may be run using competitive or non-competitive formats, and using a wide variety of labels, such as radioisotopes, enzymes, fluorescers, chemiluminescers, spin labels, and the like. A majority of suitable assays rely on heterogeneous protocols where the ligand is bound to a solid phase which is utilized to separate the ligand-autoantibody complex which forms when autoantibody is present in the serum sample. A particular advantage of using a purified ligand is that it facilitates the preparation of a solid phase for use in the assay. That is, the ligand may be conveniently immobilized on a variety of solid phases, such as dipsticks, particulates, microspheres, magnetic particles, test tubes, microtiter wells, and the like.

The solid phase is exposed to the serum sample so that the autoantibody, if any, is captured by the ligand. By then removing the solid phase from the serum sample, the captured autoantibodies can be removed from unbound autoantibodies and other contaminants in the serum sample. The captured autoantibody may then be detected using the non-competitive "sandwich" technique where labeled ligand for the autoantibody is exposed to the washed solid phase. Alternatively, competitive formats rely on the prior introduction of soluble, labeled autoantibody to the serum sample so that labeled and unlabelled forms may compete for binding to the solid phase. Such assay techniques are well known and well described in both the patent and scientific literature. Exemplary immunoassays which are suitable for detecting the autoantibodies in serum include those described in U.S. Pat. Nos. 3,791,932; 3,817,837; 3,839, 153; ,850,752; 3,850,578; 3,853,987; 3,867,517; 3,879,262; 3,901,654; 3,935,074; 3,984,533; 3,996,345; 4,034,074; and 4,098,876, the disclosures of which are incorporated herein by reference.

Particularly preferred are sensitive enzyme-linked immunosorbent assay (ELISA) methods which are described in detail in U.S. Pat. Nos. 3,791,932; 3,839,153; 3,850,752; 3,879,262; and 4,034,074. Such ELISA assays can provide measurement of very low titers of the autoantibodies.

According to the preferred ELISA technique, the purified ligand is bound either covalently or non-covalently to a solid surface. The solid surface is exposed to the serum sample where autoantibody present in the sample is captured and bound. Typically, the ligand on the solid phase will be present in excess so that the entire quantity of autoantibody may be bound. After separating the solid phase and washing its surface, the solid phase can be exposed to labeled reagent capable of specifically binding the captured autoantibody. The labeled reagent may be labeled purified ligand, or may be other ligand capable of binding to the autoantibody, e.g., labeled anti-human antibody. In this way, label is bound to the solid phase only if autoantibody was present in the serum sample. The enzyme labels may be detected by conventional visualization techniques, i.e., production of a colored dye, chemiluminescence, fluorescence, or the like.

A second preferred embodiment comprises radioimmunoassays (RIA) which are performed using a solid phase which has been prepared as described above. The solid phase is exposed to the serum sample in the presence of radiolabeled autoantibodies which can compete for binding to the immobilized ligand. In this way, the amount of radiolabel bound to the solid phase will be inversely proportional to the amount of autoantibodies initially present in the serum sample. After separation of the solid phase, non-specifically bound radiolabel can be removed by washing, and the amount of radiolabel bound to the solid phase determined. The amount of bound radiolabel, in turn, can be related to the amount of autoantibodies initially present in the sample.

Purified ligand of the present invention can be incorporated as components of pharmaceutical compositions useful to attenuate, inhibit, or prevent the destruction of pancreatic β-cells associated with the onset of insulin-dependent diabetes mellitus. The compositions should contain a therapeutic or prophylactic amount of at least one purified ligand according to the present invention in a pharmaceutically-acceptable carrier. The pharmaceutical carrier can be any compatible, non-toxic substance suitable to deliver the peptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions. Such compositions can contain nucleic acids or a single polypeptide encoded by the βIV-spectrin gene, or may contain two or more polypeptides according to the present invention in the form of a "cocktail". In one embodiment, the purified ligand binds to a protein having an amino acid sequence comprising at least one sequence of Glu-Arg-Gln-Glu-Ser (SEQ ID NO:3).

It is presently believed by the inventors herein that the destruction of pancreatic β-cells in IDDM is a cellular autoimmune response. Thus, the pharmaceutical compositions should be suitable for inhibiting such a response. In particular, it may be desirable to couple the purified ligands of the present invention to immunoglobulins, e.g., IgG, or to lymphoid cells from the patient being treated in order to promote tolerance. Such an approach is described in Bradley-Mullen, *Activation of Distinct Subsets of T Suppressor Cells with Type III Pneumococcal Polysaccharide Coupled to Syngeneic Spleen Cells*, in: IMMUNOLOGICAL TOLERANCE TO SELF AND NON-SELF, Buttisto et al., eds., Annals N.Y. Acad. Sci., Vol. 392, pp. 156–166 (1982). Alternatively, the peptides may be modified to maintain or enhance binding to the MHC while reducing or eliminating binding to the associated T-cell receptor. In this way, the modified βIV-spectrin peptides may compete with natural βIV-spectrin to inhibit helper T-cell activation and thus inhibit the immune response In all cases, care should be taken that administration of the pharmaceutical compositions of the present invention does not potentiate the autoimmune response.

The pharmaceutical compositions just described are useful for parenteral administration. Preferably, the compositions will be administered parenterally, i.e., subcutaneously, intramuscularly, or intravenously. Thus, the invention provides compositions for parenteral administration to a patient, where the compositions comprise a solution or dispersion of the polypeptides in an acceptable carrier, as described above. The concentration of the nucleic acids or polypeptides in the pharmaceutical composition can vary widely, i.e., from less than about 0.1% by weight, usually being at least about 1% by weight in as much as 20% by weight or more. Typical pharmaceutical composition for intramuscular injection would be made up to contain, for example, 1 ml of sterile buffered water and 1 to 100 μg of the purified ligand of the present invention. A typical composition for intravenous infusion could be made up to contain 100 to 500 ml of sterile Ringer's solution and 100 to 500 mg of the purified ligand. Actual methods for preparing parenterally administrable compositions are well known in the art and described in more detail in various sources, including, for example, *Remington's Pharmaceutical Science*, 15th Edition, Mack Publishing Company, Easton, Pa. (1980), which is incorporated herein by reference.

The pharmaceutical nucleic acid or polypeptide compositions of the present invention may be administered for prophylactic treatment of prediabetic individuals identified by the assay methods of the present invention or for therapeutic treatment of individuals suffering from insulin-dependent diabetes mellitus but having a substantial residual mass of pancreatic β-cells. For therapeutic applications, the pharmaceutical compositions are administered to a patient suffering from established diabetes in an amount sufficient to inhibit or prevent further β-cell destruction. For individuals susceptible to diabetes, the pharmaceutical compositions are administered prophylactically in an amount sufficient to either prevent or inhibit immune destruction of the β-cells. An amount adequate to accomplish this is defined as "therapeutically-effective dose". Such effective dosage will depend on the severity of the autoimmune response and on the general state of the patient's health, but will generally range from about 1 to 500 mg of purified ligand per kilogram of body weight, with dosages of from about 5 to 25 mg per kilogram being more commonly employed.

Figure 10:
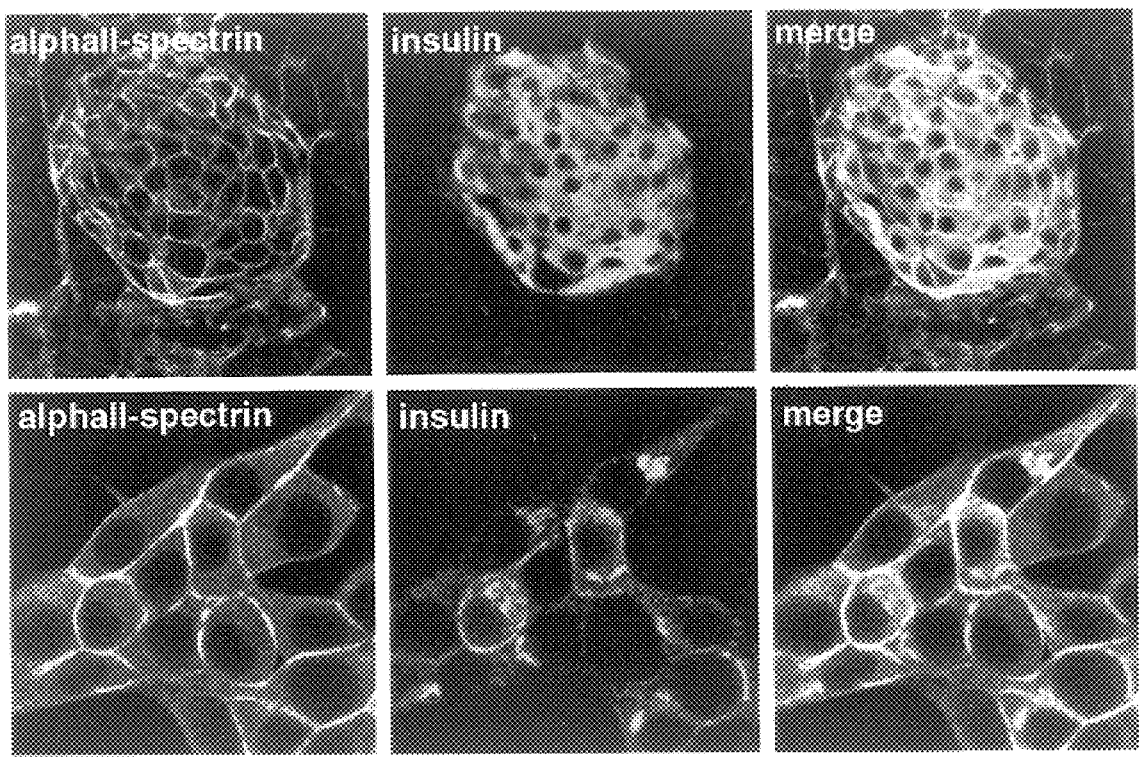
FIG. 10 is a photograph showing expression of αII spectrin in pancreatic islet cells.

The therapeutic methods of the present invention comprise administering the pharmaceutical compositions of the present invention in the amounts and under the circumstances described above.

αII spectrin may also become a candidate for targeted therapy of insulin dependent diabetes mellitus, and has been identified as being expressed in pancreatic beta cells (Haneji et al., Science 276:804 (1997); Yanagi et al., Eur. J. Immunol. 28:3336 (1998)), FIG. 10. In FIG. 10, immunocytochemistry and confocal microscopy were performed as described above for FIG. 9.

The top row of images in FIG. 10 shows expression of αII spectrin in pancreatic islets of a 6 weeks old non-obese diabetic (NOD) mouse as revealed by double immunocytochemistry with a rabbit antibody directed against αII spectrin (in green, left panel) and guinea pig anti-insulin antibody, (in red, middle panel). The merge of these two panels is shown the on the right. As shown in FIG. 10, alpha II spectrin is prominently expressed in the insulin-producing beta cells of the pancreatic islets. As shown in other cell types, the protein is primarily localized beneath the plasma membrane and mostly at regions of cell—cell contact.

The bottom row of images shown in FIG. 10 show double immunocytochemistry for αII spectrin (in green, left panel) and insulin (red, middle panel) in rat insulinoma INS-1 cells in culture. The merge of these two panels is shown in the right panel. The data shown in FIG. 10 illustrates αII spectrin is enriched in pancreatic beta cells.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

SEQUENCE LISTING

<160> NUMBER OF SEQ ID NOS: 8

<210> SEQ ID NO 1
<211> LENGTH: 7812
<212> TYPE: DNA
<213> ORGANISM: Human
<220> FEATURE:
<221> NAME/KEY: CDS
<222> LOCATION: (1)...(6879)
<221> NAME/KEY: unsure
<222> LOCATION: (100)...(102)
<221> NAME/KEY: unsure
<222> LOCATION: (1021)...(1023)
<221> NAME/KEY: unsure
<222> LOCATION: (2266)...(2268)

<400> SEQUENCE: 1

```
cta ctg gtc tct ttc tac cac tat ttc tcc aag atg aaa gct ctg gct     48
Leu Leu Val Ser Phe Tyr His Tyr Phe Ser Lys Met Lys Ala Leu Ala
 1               5                  10                  15 gtg gag ggg aaa gcc gta tcg gga agg gcc tgg atc cac cgc acc gtg     96
Val Glu Gly Lys Ala Val Ser Gly Arg Ala Trp Ile His Arg Thr Val
             20                  25                  30 ggc ntc atc agc aat cag aaa ttt gcc aac tcc tta agt ggg gtg cag    144
Gly Xaa Ile Ser Asn Gln Lys Phe Ala Asn Ser Leu Ser Gly Val Gln
         35                  40                  45 cag caa ctc cag gct ttc acg gcc tat tgc acg ctg gag aag cct gtc    192
Gln Gln Leu Gln Ala Phe Thr Ala Tyr Cys Thr Leu Glu Lys Pro Val
     50                  55                  60 aag ttc cag gag aag ggg aac cta gag gtg ctc ttc agc atc cag        240
Lys Phe Gln Glu Lys Gly Asn Leu Glu Val Leu Leu Phe Ser Ile Gln
 65                  70                  75                  80 agc aaa ctg cgt gcc tgc aac cgt cgc ctc ttt gtg cct cgg gag ggc    288
Ser Lys Leu Arg Ala Cys Asn Arg Arg Leu Phe Val Pro Arg Glu Gly
                 85                  90                  95 tgt ggc atc tgg gat att gac aag gca tgg ggt gag ctg gag aag gct    336
Cys Gly Ile Trp Asp Ile Asp Lys Ala Trp Gly Glu Leu Glu Lys Ala
            100                 105                 110 gag cat gag cgg gag gct gcc cta cgg gct gag ctg att cgg cag gag    384
Glu His Glu Arg Glu Ala Ala Leu Arg Ala Glu Leu Ile Arg Gln Glu
        115                 120                 125 aag ctg gaa cta ctg gca cag agg ttt gac cac aag gtg gct atg agg    432
Lys Leu Glu Leu Leu Ala Gln Arg Phe Asp His Lys Val Ala Met Arg
    130                 135                 140 gag agc tgg ctg aat gag aac cag cgt ctg gtc tcc cag gac aac ttt    480
Glu Ser Trp Leu Asn Glu Asn Gln Arg Leu Val Ser Gln Asp Asn Phe
145                 150                 155                 160 ggg tat gag ctg ccc gca gtg gag gca gcc atg aag aaa cac gaa gcg    528
Gly Tyr Glu Leu Pro Ala Val Glu Ala Ala Met Lys Lys His Glu Ala
                165                 170                 175 atc gag gca gac att gcg gcc tac gag gag cgg gtg cag ggt gtg gcg    576
Ile Glu Ala Asp Ile Ala Ala Tyr Glu Glu Arg Val Gln Gly Val Ala
            180                 185                 190 gag ctg gcc cag gca ttg gca gcc gaa ggc tac tac gat atc cgg cgg    624
Glu Leu Ala Gln Ala Leu Ala Ala Glu Gly Tyr Tyr Asp Ile Arg Arg
        195                 200                 205 gtg gca gcc cag cgt gac agc gtc ctc gcc cag tgg gcc ctg cta act    672
Val Ala Ala Gln Arg Asp Ser Val Leu Arg Gln Trp Ala Leu Leu Thr
    210                 215                 220 ggg ctt gtg ggt gcc cgg cgg aca cga ctt gag cag aac ctt gcc ctg    720
Gly Leu Val Gly Ala Arg Arg Thr Arg Leu Glu Gln Asn Leu Ala Leu
```

```
                    225                 230                 235                 240
cag aag gtc ttc cag gag atg gtg tac atg gtg gac tgg atg gag gag              768
Gln Lys Val Phe Gln Glu Met Val Tyr Met Val Asp Trp Met Glu Glu
                245                 250                 255 atg cag gct cag ctg ctg tcc cgg gag tgt ggg cag cac ctg gtg gag              816
Met Gln Ala Gln Leu Leu Ser Arg Glu Cys Gly Gln His Leu Val Glu
            260                 265                 270 gca gac gac ctg ttg cag aag cat gga ctg ctg gag gga gac att gcc              864
Ala Asp Asp Leu Leu Gln Lys His Gly Leu Leu Glu Gly Asp Ile Ala
        275                 280                 285 gcc cag agc gag cgg gtg gag gct ctc aat gcc gct gcc ctg cgc ttc              912
Ala Gln Ser Glu Arg Val Glu Ala Leu Asn Ala Ala Ala Leu Arg Phe
    290                 295                 300 tcc cag ccc tgc gac ccg cag gtc atc tgc aac cgc gtg aac cac gtg              960
Ser Gln Pro Cys Asp Pro Gln Val Ile Cys Asn Arg Val Asn His Val
305                 310                 315                 320 cac ggc tgc ctg gcg gag ctg cag gag cag gca gcg cgg cga cgc gcg             1008
His Gly Cys Leu Ala Glu Leu Gln Glu Gln Ala Ala Arg Arg Arg Ala
                325                 330                 335 gag ctg gag gct tcn cgg agc ctg tgg gcg ctg ctg cag gag ctg gag             1056
Glu Leu Glu Ala Xaa Arg Ser Leu Trp Ala Leu Leu Gln Glu Leu Glu
            340                 345                 350 gag gcc gag agc tgg gcg cgc gac aag gag cgt ctc ctg gag gct gcg             1104
Glu Ala Glu Ser Trp Ala Arg Asp Lys Glu Arg Leu Leu Glu Ala Ala
        355                 360                 365 ggc ggc ggc ggt gcg gcg ggc gca gcg ggc gca gcg gga aca gcg ggc             1152
Gly Gly Gly Gly Ala Ala Gly Ala Ala Gly Ala Ala Gly Thr Ala Gly
    370                 375                 380 ggc gcg cat gac ctg tcc agc aca gcg cgc ctc ctg gcc cag cac aag             1200
Gly Ala His Asp Leu Ser Ser Thr Ala Arg Leu Leu Ala Gln His Lys
385                 390                 395                 400 atc ctg cag ggc gag ctg ggc ggg cgg cga gcg tcg ctg cag cag gcc             1248
Ile Leu Gln Gly Glu Leu Gly Gly Arg Arg Ala Ser Leu Gln Gln Ala
                405                 410                 415 ctg cgg tgt ggc gag gag ctg gtt gcg gcc ggc ggt gcc gtc ggc ccg             1296
Leu Arg Cys Gly Glu Glu Leu Val Ala Ala Gly Gly Ala Val Gly Pro
            420                 425                 430 gga gca gac acc gtg cac ctg gta ggc ctg gcg gag cgc gcg gcg agc             1344
Gly Ala Asp Thr Val His Leu Val Gly Leu Ala Glu Arg Ala Ala Ser
        435                 440                 445 gcc cgg cgc cgc tgg cag agg ctg gaa gag gcg gcg gcg cgg cga gag             1392
Ala Arg Arg Arg Trp Gln Arg Leu Glu Glu Ala Ala Ala Arg Arg Glu
    450                 455                 460 cgg cgg ctg cag gag gcg cgg gcg ctg cac cag ttc ggc gct gac ctc             1440
Arg Arg Leu Gln Glu Ala Arg Ala Leu His Gln Phe Gly Ala Asp Leu
465                 470                 475                 480 gac ggg ctg ctg gac tgg ctt cgc gac gct tac cgc ctg gca gcc gcc             1488
Asp Gly Leu Leu Asp Trp Leu Arg Asp Ala Tyr Arg Leu Ala Ala Ala
                485                 490                 495 ggt gac ttc ggc cac gac gaa gct tcc agc cgc cgc ctg gcg cgc cag             1536
Gly Asp Phe Gly His Asp Glu Ala Ser Ser Arg Arg Leu Ala Arg Gln
            500                 505                 510 cac cgc gcg ctc acc ggg gag gtg gag gca cat cgc ggg ccc gtg agc             1584
His Arg Ala Leu Thr Gly Glu Val Glu Ala His Arg Gly Pro Val Ser
        515                 520                 525 ggc ctg cgg cgc cag ctg gcg aca ctc ggg ggt gcc agt ggc gca ggg             1632
Gly Leu Arg Arg Gln Leu Ala Thr Leu Gly Gly Ala Ser Gly Ala Gly
    530                 535                 540 cca ctg gtg gtg gcg ctg cag gtg cgc gtg gtg gaa gca gag cag ttg             1680
```

```
Pro Leu Val Val Ala Leu Gln Val Arg Val Glu Ala Glu Gln Leu
545                 550                 555                 560 ttc gct gag gtg acc gaa gtg gcg gcg ctg agg cgc cag tgg ctg cgg        1728
Phe Ala Glu Val Thr Glu Val Ala Ala Leu Arg Arg Gln Trp Leu Arg
                    565                 570                 575 gac gcg ctc gct gtc tac cgc atg ttt ggc gag gtg cac gcg tgt gag        1776
Asp Ala Leu Ala Val Tyr Arg Met Phe Gly Glu Val His Ala Cys Glu
                580                 585                 590 ctg tgg atc ggc gag aag gag caa tgg ctg ctc tcc atg cgt gtg ccg        1824
Leu Trp Ile Gly Glu Lys Glu Gln Trp Leu Leu Ser Met Arg Val Pro
            595                 600                 605 gat tca ctc gac gac gtc gag gtg gtg cag cac cga ttc gag agc ctg        1872
Asp Ser Leu Asp Asp Val Glu Val Val Gln His Arg Phe Glu Ser Leu
        610                 615                 620 gac caa gag atg aac agc ctg atg ggc cgc gtt ctg gac gtg aac cac        1920
Asp Gln Glu Met Asn Ser Leu Met Gly Arg Val Leu Asp Val Asn His
625                 630                 635                 640 aca gtc cag gag ctg gtg gaa gga ggc cac ccc agt tca gat gag gtg        1968
Thr Val Gln Glu Leu Val Glu Gly Gly His Pro Ser Ser Asp Glu Val
                645                 650                 655 cgt tcc tgc cag gac cac ctc aac agc agg tgg aac cgc atc gtg gag        2016
Arg Ser Cys Gln Asp His Leu Asn Ser Arg Trp Asn Arg Ile Val Glu
                660                 665                 670 cta gtg gaa cag cgc aaa gag gaa atg agc gcg gtg ctg ctg gtg gag        2064
Leu Val Glu Gln Arg Lys Glu Glu Met Ser Ala Val Leu Leu Val Glu
            675                 680                 685 aac cac gtg ctg gag gtg gcc gag gtg cgc gcc cag gtg cgt gag aag        2112
Asn His Val Leu Glu Val Ala Glu Val Arg Ala Gln Val Arg Glu Lys
        690                 695                 700 cgg aga gct gtg gag agc gcg ccc cgg gcc ggc ggc gcc ctg cag tgg        2160
Arg Arg Ala Val Glu Ser Ala Pro Arg Ala Gly Gly Ala Leu Gln Trp
705                 710                 715                 720 cgt ctt agc ggc cta gag gcc gct ctg cag gcg ctg gag ccg cgc cag        2208
Arg Leu Ser Gly Leu Glu Ala Ala Leu Gln Ala Leu Glu Pro Arg Gln
                725                 730                 735 gcg gcc ctt ctg gag gag gca gcc ctg ctg gct gag cgc ttc ccg gcg        2256
Ala Ala Leu Leu Glu Glu Ala Ala Leu Leu Ala Glu Arg Phe Pro Ala
                740                 745                 750 cag gcg gcg ngg ctg cac cag ggc gcg gag gag ctg ggc gcc gag tgg        2304
Gln Ala Ala Xaa Leu His Gln Gly Ala Glu Glu Leu Gly Ala Glu Trp
            755                 760                 765 ggc gcg cta gct agc gcg gct cag gcc tgc ggc gag gcg gtg gcg gca        2352
Gly Ala Leu Ala Ser Ala Ala Gln Ala Cys Gly Glu Ala Val Ala Ala
        770                 775                 780 gca ggg cgc ctg cag cgc ttc cta cat gac ctc gac gct ttc ctg gac        2400
Ala Gly Arg Leu Gln Arg Phe Leu His Asp Leu Asp Ala Phe Leu Asp
785                 790                 795                 800 tgg ctc gtg cgc gcc cag gag gcg gcg ggc ggc agc gag ggg ccc ctg        2448
Trp Leu Val Arg Ala Gln Glu Ala Ala Gly Gly Ser Glu Gly Pro Leu
                805                 810                 815 ccc aac agc cta gaa gag gcg gac gcg ctg ctg gcg cgc cac gct gcg        2496
Pro Asn Ser Leu Glu Glu Ala Asp Ala Leu Leu Ala Arg His Ala Ala
                820                 825                 830 ctc aag gag gag gtg gac cag cgc gag gaa gac tat gct cgc atc gtg        2544
Leu Lys Glu Glu Val Asp Gln Arg Glu Glu Asp Tyr Ala Arg Ile Val
            835                 840                 845 gcg gcc agc gag gcg ctg ctg gcc gcc gac ggc gca gag ctg ggc ccg        2592
Ala Ala Ser Glu Ala Leu Leu Ala Ala Asp Gly Ala Glu Leu Gly Pro
        850                 855                 860
```

```
ggc ctg gca cta gac gag tgg ctg cca cac ctc gaa ctt ggc tgg cat       2640
Gly Leu Ala Leu Asp Glu Trp Leu Pro His Leu Glu Leu Gly Trp His
865                 870                 875                 880 aaa ctg ctc ggc ttg tgg aag gcg cgc agg aag gcg ctg gtc cag gcg       2688
Lys Leu Leu Gly Leu Trp Lys Ala Arg Arg Lys Ala Leu Val Gln Ala
                885                 890                 895 cac atc tac cag ctc ttc ctg cgg gat cta cgc cag gcg ctc gtg gtg       2736
His Ile Tyr Gln Leu Phe Leu Arg Asp Leu Arg Gln Ala Leu Val Val
        900                 905                 910 ctg cgt aac cag gag atg gcg ctg tct ggt gcg gag ctc ccg ggc aca       2784
Leu Arg Asn Gln Glu Met Ala Leu Ser Gly Ala Glu Leu Pro Gly Thr
            915                 920                 925 gtg gaa tcg gtg gag gag gcc ttg aaa cag cac cgt gac ttt ctc acc       2832
Val Glu Ser Val Glu Glu Ala Leu Lys Gln His Arg Asp Phe Leu Thr
    930                 935                 940 acc atg gag ctg agc cag caa aag atg cag gtg gcc gtg cag gct gca       2880
Thr Met Glu Leu Ser Gln Gln Lys Met Gln Val Ala Val Gln Ala Ala
945                 950                 955                 960 gag ggc ctg ctg agg cag ggc aac atc tac ggg gag cag gct cag gag       2928
Glu Gly Leu Leu Arg Gln Gly Asn Ile Tyr Gly Glu Gln Ala Gln Glu
                965                 970                 975 gct gtg acc cgg ctg ctg gag aag aac caa gaa aac cag tta cgg gcc       2976
Ala Val Thr Arg Leu Leu Glu Lys Asn Gln Glu Asn Gln Leu Arg Ala
        980                 985                 990 cag caa tgg atg caa aag cta cat gac caa ctt gag ctg cag cac ttc       3024
Gln Gln Trp Met Gln Lys Leu His Asp Gln Leu Glu Leu Gln His Phe
            995                 1000                1005 ctc cga gac tgc cac gag ctg gat ggc tgg atc cat gag aag atg ctg       3072
Leu Arg Asp Cys His Glu Leu Asp Gly Trp Ile His Glu Lys Met Leu
    1010                1015                1020 atg gcg cgg gat ggc acg cgg gag gac aac cac aag ctg cat aag aga       3120
Met Ala Arg Asp Gly Thr Arg Glu Asp Asn His Lys Leu His Lys Arg
1025                1030                1035                1040 tgg ctc cgg cac cag gca ttc atg gcc gag ctg gct cag aat aag gag       3168
Trp Leu Arg His Gln Ala Phe Met Ala Glu Leu Ala Gln Asn Lys Glu
                1045                1050                1055 tgg ctg gag aag atc gag cgg gag ggc cca gca act gat gca gga gaa       3216
Trp Leu Glu Lys Ile Glu Arg Glu Gly Pro Ala Thr Asp Ala Gly Glu
        1060                1065                1070 gcc cga act ggc ggc ctc cgt gcg gaa gaa gct ggg cga gat ccg cca       3264
Ala Arg Thr Gly Gly Leu Arg Ala Glu Glu Ala Gly Arg Asp Pro Pro
            1075                1080                1085 gtg ctg ggc gga gct gga gag cac cac cca ggc cca agg cac ggc agc       3312
Val Leu Gly Gly Ala Gly Glu His His Pro Gly Pro Arg His Gly Ser
    1090                1095                1100 tct ttg agg ccc agc aaa gca gac cag ctg gtg cag agc ttt gct gag       3360
Ser Leu Arg Pro Ser Lys Ala Asp Gln Leu Val Gln Ser Phe Ala Glu
1105                1110                1115                1120 ctg gac aag aag ctc ctt cac atg gag agc cag ctg caa gac gtg gac       3408
Leu Asp Lys Lys Leu Leu His Met Glu Ser Gln Leu Gln Asp Val Asp
                1125                1130                1135 cct gga gga gac ctg gcc act gtc aac agt cag ctc aag aag ctg cag       3456
Pro Gly Gly Asp Leu Ala Thr Val Asn Ser Gln Leu Lys Lys Leu Gln
        1140                1145                1150 tcc atg gag tcg cag gtg gag gag tgg tac cgc gag gtg gga gag ctg       3504
Ser Met Glu Ser Gln Val Glu Glu Trp Tyr Arg Glu Val Gly Glu Leu
            1155                1160                1165 cag gcg cag acg gcg gcg ctg ccg ctg gag ccg gcg agc aag gag ctg       3552
Gln Ala Gln Thr Ala Ala Leu Pro Leu Glu Pro Ala Ser Lys Glu Leu
    1170                1175                1180
```

```
gtg ggt gag cgg cag aac gcg gtg ggc gag cgc ctg gtg cgc ctg ctc    3600
Val Gly Glu Arg Gln Asn Ala Val Gly Glu Arg Leu Val Arg Leu Leu
        1185                1190                1195            1200 gag ccg ttg cag gag cgc cgc cgc ttg ctg ctg gct tcc aag gag ttg    3648
Glu Pro Leu Gln Glu Arg Arg Arg Leu Leu Leu Ala Ser Lys Glu Leu
                1205                1210                1215 cac cag gtg gcg cac gac ctg gac gac gag ctg gca tgg gtt cag gag    3696
His Gln Val Ala His Asp Leu Asp Asp Glu Leu Ala Trp Val Gln Glu
            1220                1225                1230 cgg ctg cca ctg gcc atg cag aca gag cga ggc aac ggt ttg cag gcg    3744
Arg Leu Pro Leu Ala Met Gln Thr Glu Arg Gly Asn Gly Leu Gln Ala
        1235                1240                1245 gtc cag cag cac atc aaa aag aac cag ggc ctg cgg cgg gag atc cag    3792
Val Gln Gln His Ile Lys Lys Asn Gln Gly Leu Arg Arg Glu Ile Gln
    1250                1255                1260 gcg cat ggg ccg cgc ctg gag gag gtg ctg gag cgc gcg ggc gcg ctg    3840
Ala His Gly Pro Arg Leu Glu Glu Val Leu Glu Arg Ala Gly Ala Leu
1265                1270                1275                1280 gcg tcg ctg cgc agc ccg gag gca gag gca gtg cgc cgg ggc ctg gag    3888
Ala Ser Leu Arg Ser Pro Glu Ala Glu Ala Val Arg Arg Gly Leu Glu
                1285                1290                1295 cag ctg cag agc gcc tgg gcc gga ctg cgg gag gct gcc gag cga cgg    3936
Gln Leu Gln Ser Ala Trp Ala Gly Leu Arg Glu Ala Ala Glu Arg Arg
            1300                1305                1310 cag cag gtg ctg gac gcc gcc ttc cag gtg gag cag tac tac ttc gac    3984
Gln Gln Val Leu Asp Ala Ala Phe Gln Val Glu Gln Tyr Tyr Phe Asp
        1315                1320                1325 gtg gct gag gtg gag gcg tgg ctg ggc gag cag gag ctg ctc atg atg    4032
Val Ala Glu Val Glu Ala Trp Leu Gly Glu Gln Glu Leu Leu Met Met
    1330                1335                1340 agt gag gac aag ggc aag gtg cgc ccg agc tgg ggg tgc gga ggg cct    4080
Ser Glu Asp Lys Gly Lys Val Arg Pro Ser Trp Gly Cys Gly Gly Pro
1345                1350                1355                1360 ggg ggc gct gga gcc ggg ggc cgc cgc tgc cgc ctc atc gtg ggc gct    4128
Gly Gly Ala Gly Ala Gly Gly Arg Arg Cys Arg Leu Ile Val Gly Ala
                1365                1370                1375 ttg tgc ccc cag gac gaa cag agc acc ctg cag ctg ctc aag aaa cac    4176
Leu Cys Pro Gln Asp Glu Gln Ser Thr Leu Gln Leu Leu Lys Lys His
            1380                1385                1390 ctg cag ctg gag caa ggc gtg gag aac tac gag gaa agc atc gcg cag    4224
Leu Gln Leu Glu Gln Gly Val Glu Asn Tyr Glu Glu Ser Ile Ala Gln
        1395                1400                1405 ctg tcg cgc cag tgc cgg gcg ctg ctg gag atg ggg cac ccg gac agc    4272
Leu Ser Arg Gln Cys Arg Ala Leu Leu Glu Met Gly His Pro Asp Ser
    1410                1415                1420 gag cag atc agc cgg cgg cag tct cag gtg gac cgc ctg tac gtg gcg    4320
Glu Gln Ile Ser Arg Arg Gln Ser Gln Val Asp Arg Leu Tyr Val Ala
1425                1430                1435                1440 ctc aag gag ctg ggt gag gag cgc cgg gtg gct ctg gaa cag cag tac    4368
Leu Lys Glu Leu Gly Glu Glu Arg Arg Val Ala Leu Glu Gln Gln Tyr
                1445                1450                1455 tgg ctg tac cag ctc agc cgc cag gtg agc gag ctt gag cac tgg att    4416
Trp Leu Tyr Gln Leu Ser Arg Gln Val Ser Glu Leu Glu His Trp Ile
            1460                1465                1470 gcc gag aag gag gtg gtg gct ggc tca ccc gag ctc ggc cag gac ttt    4464
Ala Glu Lys Glu Val Val Ala Gly Ser Pro Glu Leu Gly Gln Asp Phe
        1475                1480                1485 gag cat gtc tcg gtg ctg cag gag aaa ttc tca gag ttt gcc agc gag    4512
Glu His Val Ser Val Leu Gln Glu Lys Phe Ser Glu Phe Ala Ser Glu
```

|  |  |
|---|---|
| aca ggt atg gca ggg cgg gaa cgg ctg gca gct gtg aac cag atg gtg<br>Thr Gly Met Ala Gly Arg Glu Arg Leu Ala Ala Val Asn Gln Met Val<br>1505                              1510                       1515                       1520 | 4560 |
| gat gag ctg atc gag tgt ggc cat aca gca gcg gcc acc atg gcc gag<br>Asp Glu Leu Ile Glu Cys Gly His Thr Ala Ala Ala Thr Met Ala Glu<br>                1525                       1530                       1535 | 4608 |
| tgg aag gac gga ctg aac gag gcc tgg gct gag ctg ctg gag ctc atg<br>Trp Lys Asp Gly Leu Asn Glu Ala Trp Ala Glu Leu Leu Glu Leu Met<br>        1540                       1545                       1550 | 4656 |
| ggc aca cgg gcc cag ctg ctg gcc gcc tct cgg gag ctt cat aag ttc<br>Gly Thr Arg Ala Gln Leu Leu Ala Ala Ser Arg Glu Leu His Lys Phe<br>                1555                       1560                       1565 | 4704 |
| ttc agt gac gcc cga gag ctt cag gga cag att gag gag aag cgg agg<br>Phe Ser Asp Ala Arg Glu Leu Gln Gly Gln Ile Glu Glu Lys Arg Arg<br>    1570                       1575                       1580 | 4752 |
| cgg ctg ccc cgc ctg acc acc ccg cct gag ccg aga ccc agt gcc agt<br>Arg Leu Pro Arg Leu Thr Thr Pro Pro Glu Pro Arg Pro Ser Ala Ser<br>1585                              1590                       1595                       1600 | 4800 |
| tcc atg cag cgg acc ctg aga gcc ttt gag cat gac ctg cag ctc ctc<br>Ser Met Gln Arg Thr Leu Arg Ala Phe Glu His Asp Leu Gln Leu Leu<br>                1605                       1610                       1615 | 4848 |
| gtg tcc cag gta cgg cag ctg cag gag ggg gcg gcc cag ctg cgg acg<br>Val Ser Gln Val Arg Gln Leu Gln Glu Gly Ala Ala Gln Leu Arg Thr<br>        1620                       1625                       1630 | 4896 |
| gtg tat gcg ggt gaa cat gcc gag gcc atc gct agc cgg gag cag gag<br>Val Tyr Ala Gly Glu His Ala Glu Ala Ile Ala Ser Arg Glu Gln Glu<br>    1635                       1640                       1645 | 4944 |
| gtg ctg cag ggt tgg aaa gag ctg ctg tca gcc tgt gag gat gcc cgc<br>Val Leu Gln Gly Trp Lys Glu Leu Leu Ser Ala Cys Glu Asp Ala Arg<br>1650                              1655                       1660 | 4992 |
| ctg cat gtc agc tcc aca gcc gac gcc ctg cgc ttc cac agc caa gtc<br>Leu His Val Ser Ser Thr Ala Asp Ala Leu Arg Phe His Ser Gln Val<br>1665                              1670                       1675                       1680 | 5040 |
| cgc gac ctg ctc tcc tgg atg gat ggc atc gcc agc cag att ggg gca<br>Arg Asp Leu Leu Ser Trp Met Asp Gly Ile Ala Ser Gln Ile Gly Ala<br>                1685                       1690                       1695 | 5088 |
| gcc gac aag ccc agg gac gtg tca tca gtg gag gtg ctc atg aac tac<br>Ala Asp Lys Pro Arg Asp Val Ser Ser Val Glu Val Leu Met Asn Tyr<br>        1700                       1705                       1710 | 5136 |
| cac cag ggc ctg aag act gag ctg gag gcg cgg gtg cct gag ctg acc<br>His Gln Gly Leu Lys Thr Glu Leu Glu Ala Arg Val Pro Glu Leu Thr<br>    1715                       1720                       1725 | 5184 |
| acc tgc cag gag ctg ggg cga tct ctg ctg ctc aac aaa agt gcc atg<br>Thr Cys Gln Glu Leu Gly Arg Ser Leu Leu Leu Asn Lys Ser Ala Met<br>1730                              1735                       1740 | 5232 |
| gct gat gag atc cag gca cag ctg gac aag ctg gga acc agg aag gag<br>Ala Asp Glu Ile Gln Ala Gln Leu Asp Lys Leu Gly Thr Arg Lys Glu<br>1745                              1750                       1755                       1760 | 5280 |
| gag gtg tcg gaa aag tgg gac cgc cat tgg gag tgg ctg cag cag atg<br>Glu Val Ser Glu Lys Trp Asp Arg His Trp Glu Trp Leu Gln Gln Met<br>                1765                       1770                       1775 | 5328 |
| ctg gag gtg cac cag ttt gcc cag gag gcg gtg gtg gct gat gcc tgg<br>Leu Glu Val His Gln Phe Ala Gln Glu Ala Val Val Ala Asp Ala Trp<br>        1780                       1785                       1790 | 5376 |
| ctg aca gcc cag gag ccg ctc ctg cag agc cgg gag ctg ggc agc agc<br>Leu Thr Ala Gln Glu Pro Leu Leu Gln Ser Arg Glu Leu Gly Ser Ser<br>    1795                       1800                       1805 | 5424 |
| gtg gat gag gtg gag cag ctt atc cgg cga cat gag gcc ttc cgc aaa | 5472 |

```
                 -continued

Val Asp Glu Val Glu Gln Leu Ile Arg Arg His Glu Ala Phe Arg Lys
    1810            1815                1820 gcg gct gca gcc tgg gaa gag agg ttc agc tct ctg cgg cgc ctg acc    5520
Ala Ala Ala Ala Trp Glu Glu Arg Phe Ser Ser Leu Arg Arg Leu Thr
1825            1830                1835                1840 acg atc gag aaa atc aaa gcg gaa cag agc aag cag ccg cct acc cca    5568
Thr Ile Glu Lys Ile Lys Ala Glu Gln Ser Lys Gln Pro Pro Thr Pro
                1845                1850                1855 ctg ctg ggg cgc aag ttc ttt ggg gac ccc acg gaa ctg gcg gcc aag    5616
Leu Leu Gly Arg Lys Phe Phe Gly Asp Pro Thr Glu Leu Ala Ala Lys
            1860                1865                1870 gcg gcg ccc ctg ctg cgg cca ggg ggc tat gaa agg ggc ttg gag ccc    5664
Ala Ala Pro Leu Leu Arg Pro Gly Gly Tyr Glu Arg Gly Leu Glu Pro
        1875                1880                1885 ctg gcc cgc cga gcc tcg gac acg ctc tcg gcc gag gtg cgg act cgg    5712
Leu Ala Arg Arg Ala Ser Asp Thr Leu Ser Ala Glu Val Arg Thr Arg
    1890                1895                1900 gtg ggg tat gtg cgc cag gag ctc aag ccc gag cgc ctc cag ccg cgc    5760
Val Gly Tyr Val Arg Gln Glu Leu Lys Pro Glu Arg Leu Gln Pro Arg
1905            1910                1915                1920 att gac cgg ctg ccg gag atc ccg ggg agg gtg gag ccc gcg gcc ctg    5808
Ile Asp Arg Leu Pro Glu Ile Pro Gly Arg Val Glu Pro Ala Ala Leu
                1925                1930                1935 ccg gcc gca cca gag gac gcg gcg gag acc ccc gcg acc ccc gcg gcg    5856
Pro Ala Ala Pro Glu Asp Ala Ala Glu Thr Pro Ala Thr Pro Ala Ala
            1940                1945                1950 gcg gag cag gtg cgg cca cga ccg gag cgc cag gag tca gct gat cgc    5904
Ala Glu Gln Val Arg Pro Arg Pro Glu Arg Gln Glu Ser Ala Asp Arg
        1955                1960                1965 gcg gag gag ctg ccc agg agg cgg cgg cct gag cgg caa gag tca gtc    5952
Ala Glu Glu Leu Pro Arg Arg Arg Arg Pro Glu Arg Gln Glu Ser Val
    1970                1975                1980 gat caa tcc gag gag gct gcg cgg agg cgg cgg ccg gag cgg cag gag    6000
Asp Gln Ser Glu Glu Ala Ala Arg Arg Arg Arg Pro Glu Arg Gln Glu
1985            1990                1995                2000 tca gcg gag cac gag gcg gca cac agc ctt acc ctg ggc cgc tat gag    6048
Ser Ala Glu His Glu Ala Ala His Ser Leu Thr Leu Gly Arg Tyr Glu
                2005                2010                2015 cag atg gag cgg cgg cgc gag cgg cgt gag cgg cgc ttg gag cgg cag    6096
Gln Met Glu Arg Arg Arg Glu Arg Arg Glu Arg Arg Leu Glu Arg Gln
            2020                2025                2030 gag tcc agc gaa cag gag atg ccc atc aga gga gac ctg gtc aag ggg    6144
Glu Ser Ser Glu Gln Glu Met Pro Ile Arg Gly Asp Leu Val Lys Gly
        2035                2040                2045 aag gcc acc ctg gct gac att gtg gaa cag ctg cag gag aaa gag gca    6192
Lys Ala Thr Leu Ala Asp Ile Val Glu Gln Leu Gln Glu Lys Glu Ala
    2050                2055                2060 ggc cca ggg ctg cct gct ggg ccg tcg ctg cct cag cca cgc gag ctt    6240
Gly Pro Gly Leu Pro Ala Gly Pro Ser Leu Pro Gln Pro Arg Glu Leu
2065            2070                2075                2080 ccc cca ggt cgc ctg ccc aac ggg ctt gag ctg ccc gag cgg aca cct    6288
Pro Pro Gly Arg Leu Pro Asn Gly Leu Glu Leu Pro Glu Arg Thr Pro
                2085                2090                2095 cgg ccg gac cgg ccc cgg gcg cgg gac cgg ccc aag ccg cga cgg cgg    6336
Arg Pro Asp Arg Pro Arg Ala Arg Asp Arg Pro Lys Pro Arg Arg Arg
            2100                2105                2110 ccg cgg ccc aga gag ggt ggt gag ggc ggg gga agc cgg cgc tcg cgc    6384
Pro Arg Pro Arg Glu Gly Gly Glu Gly Gly Gly Ser Arg Arg Ser Arg
        2115                2120                2125
```

```
tcc gcc ccg gcc cag ggc ggc tcc gcc ccc gcg cct ccg cca ccg ccc    6432
Ser Ala Pro Ala Gln Gly Gly Ser Ala Pro Ala Pro Pro Pro Pro Pro
    2130                2135                2140 act cac aca gtg cag cac gag ggc ttc cta ctg cgc aag cgc gag ctc    6480
Thr His Thr Val Gln His Glu Gly Phe Leu Leu Arg Lys Arg Glu Leu
2145                2150                2155                2160 gac gct aac cgc aag tcg tcc aac cgg tcg tgg gtg agc ctg tac tgt    6528
Asp Ala Asn Arg Lys Ser Ser Asn Arg Ser Trp Val Ser Leu Tyr Cys
                2165                2170                2175 gtg ctt agt aag ggg gaa ctg ggc ttc tac aag gac tcc aag ggc ccg    6576
Val Leu Ser Lys Gly Glu Leu Gly Phe Tyr Lys Asp Ser Lys Gly Pro
            2180                2185                2190 gca tcc ggg agc aca cac ggt ggg gaa ccg ctg ctc agc ctg cac aag    6624
Ala Ser Gly Ser Thr His Gly Gly Glu Pro Leu Leu Ser Leu His Lys
        2195                2200                2205 gcc acc agc gag gtg gct agt gac tac aag aaa aag aag cat gtc ttc    6672
Ala Thr Ser Glu Val Ala Ser Asp Tyr Lys Lys Lys Lys His Val Phe
    2210                2215                2220 aag ctc cag acc cag gat ggc agt gag ttt ttg ctc cag gca aaa gat    6720
Lys Leu Gln Thr Gln Asp Gly Ser Glu Phe Leu Leu Gln Ala Lys Asp
2225                2230                2235                2240 gag gag gag atg aac ggc tgg ctg gag gct gta gct tcc tcg gtg gcg    6768
Glu Glu Glu Met Asn Gly Trp Leu Glu Ala Val Ala Ser Ser Val Ala
                2245                2250                2255 gaa cac gca gag atc gcc cgc tgg ggc cag aca cta ccc act act tca    6816
Glu His Ala Glu Ile Ala Arg Trp Gly Gln Thr Leu Pro Thr Thr Ser
            2260                2265                2270 tcc aca gat gag ggc aac cct aag agg gaa ggc gga gat cgc agg gcc    6864
Ser Thr Asp Glu Gly Asn Pro Lys Arg Glu Gly Gly Asp Arg Arg Ala
        2275                2280                2285 agc ggg cgc agg aag tgacttccca cccccaggac ctgacacatc tcgtctcccc    6919
Ser Gly Arg Arg Lys
    2290 tcttttccgc actgtgggca caaagacact ttttcttccg cagggggggg agcccctagt    6979 tccaacactg aggacgcgtg acatggtggg caccggaaag gagggacttt ctcctgcacc    7039 ccaagaagtg gtggggagat tgctgcccct atagccatat ctcggcccct tcccactcac    7099 caccccacc ccaggtgctg gggtccctt atttttatgc aataactgag cttgatgggg    7159 gtgggcaggg ggccagttga gccaagcccc cagccccgat ctgcagatcc tgccccaaga    7219 agctggggtg gtgggggcag taattcctgc ccccctctct gccctaggga tgggcacggg    7279 ggcgctggtg aggtcccctg gaccatccag ggtgctaggg gcagggagg ggacaccccc    7339 tccccgcctt tacctcactt ccaatgctgc cttgatctct gtctgggagg ggggagtgaa    7399 ggggccctag cccctgcac tccgccgcct cagagccatg cggttaattc ctgacttagt    7459 ttatttttgc aaaacgtcga tctcctcctc ccccgcccg catccgcgaa ggcttttaat    7519 gggagggcg tcaaagctca aaactgtttt cctctctcct ccccctcca gttgtaaatg    7579 ccacttcatg aggggagggg cgaggggaag cccacccctg catgcttctg gctgagcac    7639 ctccctgggg agtcggggga ttgggttgtg ggcagtcccc atgccgcct ggagaagccg    7699 ctggggcccg ggggtgtggg gcggtgtggc gggcgcacac tgtatgtacc tataataaac    7759 cctttggctt tgaaaaaaaa aaaaaaaaaa aaaaaaaaaa aaaaaaaaaa aaa    7812

<210> SEQ ID NO 2
<211> LENGTH: 2293
<212> TYPE: PRT
<213> ORGANISM: Human
```

<400> SEQUENCE: 2

| | | | | | | | | | | | | | | |
|---|---|---|---|---|---|---|---|---|---|---|---|---|---|---|
|Leu|Leu|Val|Ser|Phe|Tyr|His|Tyr|Phe|Ser|Lys|Met|Lys|Ala|Leu|Ala|
|1| | | |5| | | |10| | | |15| | |
|Val|Glu|Gly|Lys|Ala|Val|Ser|Gly|Arg|Ala|Trp|Ile|His|Arg|Thr|Val|
| | | |20| | | |25| | | |30| | | |
|Gly|Xaa|Ile|Ser|Asn|Gln|Lys|Phe|Ala|Asn|Ser|Leu|Ser|Gly|Val|Gln|
| | |35| | | |40| | | |45| | | | |
|Gln|Gln|Leu|Gln|Ala|Phe|Thr|Ala|Tyr|Cys|Thr|Leu|Glu|Lys|Pro|Val|
| |50| | | | |55| | | |60| | | | |
|Lys|Phe|Gln|Glu|Lys|Gly|Asn|Leu|Glu|Val|Leu|Leu|Phe|Ser|Ile|Gln|
|65| | | | |70| | | |75| | | | |80|
|Ser|Lys|Leu|Arg|Ala|Cys|Asn|Arg|Arg|Leu|Phe|Val|Pro|Arg|Glu|Gly|
| | | | |85| | | |90| | | |95| | |
|Cys|Gly|Ile|Trp|Asp|Ile|Asp|Lys|Ala|Trp|Gly|Glu|Leu|Glu|Lys|Ala|
| | | |100| | | |105| | | |110| | | |
|Glu|His|Glu|Arg|Glu|Ala|Ala|Leu|Arg|Ala|Glu|Leu|Ile|Arg|Gln|Glu|
| | |115| | | |120| | | |125| | | | |
|Lys|Leu|Glu|Leu|Leu|Ala|Gln|Arg|Phe|Asp|His|Lys|Val|Ala|Met|Arg|
| |130| | | | |135| | | |140| | | | |
|Glu|Ser|Trp|Leu|Asn|Glu|Asn|Gln|Arg|Leu|Val|Ser|Gln|Asp|Asn|Phe|
|145| | | | |150| | | |155| | | | |160|
|Gly|Tyr|Glu|Leu|Pro|Ala|Val|Glu|Ala|Ala|Met|Lys|Lys|His|Glu|Ala|
| | | | |165| | | |170| | | |175| | |
|Ile|Glu|Ala|Asp|Ile|Ala|Ala|Tyr|Glu|Glu|Arg|Val|Gln|Gly|Val|Ala|
| | | |180| | | |185| | | |190| | | |
|Glu|Leu|Ala|Gln|Ala|Leu|Ala|Ala|Glu|Gly|Tyr|Tyr|Asp|Ile|Arg|Arg|
| |195| | | | |200| | | |205| | | | |
|Val|Ala|Ala|Gln|Arg|Asp|Ser|Val|Leu|Arg|Gln|Trp|Ala|Leu|Leu|Thr|
| |210| | | | |215| | | |220| | | | |
|Gly|Leu|Val|Gly|Ala|Arg|Arg|Thr|Arg|Leu|Glu|Gln|Asn|Leu|Ala|Leu|
|225| | | | |230| | | |235| | | | |240|
|Gln|Lys|Val|Phe|Gln|Glu|Met|Val|Tyr|Met|Val|Asp|Trp|Met|Glu|Glu|
| | | | |245| | | |250| | | |255| | |
|Met|Gln|Ala|Gln|Leu|Leu|Ser|Arg|Glu|Cys|Gly|Gln|His|Leu|Val|Glu|
| | | |260| | | |265| | | |270| | | |
|Ala|Asp|Asp|Leu|Leu|Gln|Lys|His|Gly|Leu|Leu|Glu|Gly|Asp|Ile|Ala|
| | |275| | | | |280| | | |285| | | |
|Ala|Gln|Ser|Glu|Arg|Val|Glu|Ala|Leu|Asn|Ala|Ala|Ala|Leu|Arg|Phe|
| |290| | | | |295| | | |300| | | | |
|Ser|Gln|Pro|Cys|Asp|Pro|Gln|Val|Ile|Cys|Asn|Arg|Val|Asn|His|Val|
|305| | | | |310| | | |315| | | | |320|
|His|Gly|Cys|Leu|Ala|Glu|Leu|Gln|Glu|Gln|Ala|Ala|Arg|Arg|Arg|Ala|
| | | | |325| | | |330| | | |335| | |
|Glu|Leu|Glu|Ala|Xaa|Arg|Ser|Leu|Trp|Ala|Leu|Leu|Gln|Glu|Leu|Glu|
| | | |340| | | |345| | | |350| | | |
|Glu|Ala|Glu|Ser|Trp|Ala|Arg|Asp|Lys|Glu|Arg|Leu|Leu|Glu|Ala|Ala|
| |355| | | | |360| | | |365| | | | |
|Gly|Gly|Gly|Gly|Ala|Ala|Gly|Ala|Ala|Gly|Ala|Ala|Gly|Thr|Ala|Gly|
| |370| | | | |375| | | |380| | | | |
|Gly|Ala|His|Asp|Leu|Ser|Ser|Thr|Ala|Arg|Leu|Leu|Ala|Gln|His|Lys|
|385| | | | |390| | | |395| | | | |400|
|Ile|Leu|Gln|Gly|Glu|Leu|Gly|Gly|Arg|Arg|Ala|Ser|Leu|Gln|Gln|Ala|

-continued

```
                405                 410                 415
Leu Arg Cys Gly Glu Leu Val Ala Ala Gly Ala Val Gly Pro
            420                 425             430
Gly Ala Asp Thr Val His Leu Val Gly Leu Ala Glu Arg Ala Ala Ser
            435                 440                 445
Ala Arg Arg Arg Trp Gln Arg Leu Glu Glu Ala Ala Ala Arg Arg Glu
    450                 455                 460
Arg Arg Leu Gln Glu Ala Arg Ala Leu His Gln Phe Gly Ala Asp Leu
465                 470                 475                 480
Asp Gly Leu Leu Asp Trp Leu Arg Asp Ala Tyr Arg Leu Ala Ala Ala
                485                 490                 495
Gly Asp Phe Gly His Asp Glu Ala Ser Ser Arg Arg Leu Ala Arg Gln
            500                 505                 510
His Arg Ala Leu Thr Gly Glu Val Glu Ala His Arg Gly Pro Val Ser
            515                 520                 525
Gly Leu Arg Arg Gln Leu Ala Thr Leu Gly Gly Ala Ser Gly Ala Gly
    530                 535                 540
Pro Leu Val Val Ala Leu Gln Val Arg Val Glu Ala Glu Gln Leu
545                 550                 555                 560
Phe Ala Glu Val Thr Glu Val Ala Ala Leu Arg Arg Gln Trp Leu Arg
                565                 570                 575
Asp Ala Leu Ala Val Tyr Arg Met Phe Gly Glu Val His Ala Cys Glu
            580                 585                 590
Leu Trp Ile Gly Glu Lys Glu Gln Trp Leu Leu Ser Met Arg Val Pro
            595                 600                 605
Asp Ser Leu Asp Asp Val Glu Val Val Gln His Arg Phe Glu Ser Leu
    610                 615                 620
Asp Gln Glu Met Asn Ser Leu Met Gly Arg Val Leu Asp Val Asn His
625                 630                 635                 640
Thr Val Gln Glu Leu Val Glu Gly Gly His Pro Ser Ser Asp Glu Val
                645                 650                 655
Arg Ser Cys Gln Asp His Leu Asn Ser Arg Trp Asn Arg Ile Val Glu
            660                 665                 670
Leu Val Glu Gln Arg Lys Glu Glu Met Ser Ala Val Leu Leu Val Glu
            675                 680                 685
Asn His Val Leu Glu Val Ala Glu Val Arg Ala Gln Val Arg Glu Lys
    690                 695                 700
Arg Arg Ala Val Glu Ser Ala Pro Arg Ala Gly Gly Ala Leu Gln Trp
705                 710                 715                 720
Arg Leu Ser Gly Leu Glu Ala Ala Leu Gln Ala Leu Glu Pro Arg Gln
                725                 730                 735
Ala Ala Leu Leu Glu Glu Ala Ala Leu Leu Ala Glu Arg Phe Pro Ala
            740                 745                 750
Gln Ala Ala Xaa Leu His Gln Gly Ala Glu Glu Leu Gly Ala Glu Trp
            755                 760                 765
Gly Ala Leu Ala Ser Ala Ala Gln Ala Cys Gly Glu Val Ala Ala
    770                 775                 780
Ala Gly Arg Leu Gln Arg Phe Leu His Asp Leu Asp Ala Phe Leu Asp
785                 790                 795                 800
Trp Leu Val Arg Ala Gln Glu Ala Ala Gly Ser Glu Gly Pro Leu
                805                 810                 815
Pro Asn Ser Leu Glu Glu Ala Asp Ala Leu Leu Ala Arg His Ala Ala
            820                 825                 830
```

```
Leu Lys Glu Glu Val Asp Gln Arg Glu Asp Tyr Ala Arg Ile Val
        835                 840                 845
Ala Ala Ser Glu Ala Leu Leu Ala Ala Asp Gly Ala Glu Leu Gly Pro
850                 855                 860
Gly Leu Ala Leu Asp Glu Trp Leu Pro His Leu Glu Leu Gly Trp His
865                 870                 875                 880
Lys Leu Leu Gly Leu Trp Lys Ala Arg Arg Lys Ala Leu Val Gln Ala
                885                 890                 895
His Ile Tyr Gln Leu Phe Leu Arg Asp Leu Arg Gln Ala Leu Val Val
            900                 905                 910
Leu Arg Asn Gln Glu Met Ala Leu Ser Gly Ala Glu Leu Pro Gly Thr
            915                 920                 925
Val Glu Ser Val Glu Glu Ala Leu Lys Gln His Arg Asp Phe Leu Thr
            930                 935                 940
Thr Met Glu Leu Ser Gln Gln Lys Met Gln Val Ala Val Gln Ala Ala
945                 950                 955                 960
Glu Gly Leu Leu Arg Gln Gly Asn Ile Tyr Gly Glu Gln Ala Gln Glu
                965                 970                 975
Ala Val Thr Arg Leu Leu Glu Lys Asn Gln Glu Asn Gln Leu Arg Ala
            980                 985                 990
Gln Gln Trp Met Gln Lys Leu His Asp Gln Leu Glu Leu Gln His Phe
            995                 1000                1005
Leu Arg Asp Cys His Glu Leu Asp Gly Trp Ile His Glu Lys Met Leu
            1010                1015                1020
Met Ala Arg Asp Gly Thr Arg Glu Asp Asn His Lys Leu His Lys Arg
1025                1030                1035                1040
Trp Leu Arg His Gln Ala Phe Met Ala Glu Leu Ala Gln Asn Lys Glu
                1045                1050                1055
Trp Leu Glu Lys Ile Glu Arg Glu Gly Pro Ala Thr Asp Ala Gly Glu
                1060                1065                1070
Ala Arg Thr Gly Gly Leu Arg Ala Glu Glu Ala Gly Arg Asp Pro Pro
            1075                1080                1085
Val Leu Gly Gly Ala Gly Glu His His Pro Gly Pro Arg His Gly Ser
            1090                1095                1100
Ser Leu Arg Pro Ser Lys Ala Asp Gln Leu Val Gln Ser Phe Ala Glu
1105                1110                1115                1120
Leu Asp Lys Lys Leu Leu His Met Glu Ser Gln Leu Gln Asp Val Asp
                1125                1130                1135
Pro Gly Gly Asp Leu Ala Thr Val Asn Ser Gln Leu Lys Lys Leu Gln
            1140                1145                1150
Ser Met Glu Ser Gln Val Glu Glu Trp Tyr Arg Glu Val Gly Glu Leu
            1155                1160                1165
Gln Ala Gln Thr Ala Ala Leu Pro Leu Glu Pro Ala Ser Lys Glu Leu
            1170                1175                1180
Val Gly Glu Arg Gln Asn Ala Val Gly Glu Arg Leu Val Arg Leu Leu
1185                1190                1195                1200
Glu Pro Leu Gln Glu Arg Arg Arg Leu Leu Leu Ala Ser Lys Glu Leu
                1205                1210                1215
His Gln Val Ala His Asp Leu Asp Asp Glu Leu Ala Trp Val Gln Glu
            1220                1225                1230
Arg Leu Pro Leu Ala Met Gln Thr Glu Arg Gly Asn Gly Leu Gln Ala
            1235                1240                1245
```

-continued

Val Gln Gln His Ile Lys Lys Asn Gln Gly Leu Arg Arg Glu Ile Gln
    1250                1255                1260

Ala His Gly Pro Arg Leu Glu Glu Val Leu Glu Arg Ala Gly Ala Leu
1265                1270                1275                1280

Ala Ser Leu Arg Ser Pro Glu Ala Glu Val Arg Arg Gly Leu Glu
        1285                1290                1295

Gln Leu Gln Ser Ala Trp Ala Gly Leu Arg Glu Ala Glu Arg Arg
    1300                1305                1310

Gln Gln Val Leu Asp Ala Ala Phe Gln Val Glu Gln Tyr Tyr Phe Asp
    1315                1320                1325

Val Ala Glu Val Glu Ala Trp Leu Gly Glu Gln Glu Leu Leu Met Met
    1330                1335                1340

Ser Glu Asp Lys Gly Lys Val Arg Pro Ser Trp Gly Cys Gly Gly Pro
1345                1350                1355                1360

Gly Gly Ala Gly Ala Gly Gly Arg Arg Cys Arg Leu Ile Val Gly Ala
        1365                1370                1375

Leu Cys Pro Gln Asp Glu Gln Ser Thr Leu Gln Leu Leu Lys Lys His
        1380                1385                1390

Leu Gln Leu Glu Gln Gly Val Glu Asn Tyr Glu Glu Ser Ile Ala Gln
        1395                1400                1405

Leu Ser Arg Gln Cys Arg Ala Leu Leu Glu Met Gly His Pro Asp Ser
    1410                1415                1420

Glu Gln Ile Ser Arg Arg Gln Ser Gln Val Asp Arg Leu Tyr Val Ala
1425                1430                1435                1440

Leu Lys Glu Leu Gly Glu Glu Arg Arg Val Ala Leu Glu Gln Gln Tyr
        1445                1450                1455

Trp Leu Tyr Gln Leu Ser Arg Gln Val Ser Glu Leu Glu His Trp Ile
        1460                1465                1470

Ala Glu Lys Glu Val Val Ala Gly Ser Pro Glu Leu Gly Gln Asp Phe
        1475                1480                1485

Glu His Val Ser Val Leu Gln Glu Lys Phe Ser Glu Phe Ala Ser Glu
    1490                1495                1500

Thr Gly Met Ala Gly Arg Glu Arg Leu Ala Ala Val Asn Gln Met Val
1505                1510                1515                1520

Asp Glu Leu Ile Glu Cys Gly His Thr Ala Ala Thr Met Ala Glu
        1525                1530                1535

Trp Lys Asp Gly Leu Asn Glu Ala Trp Ala Glu Leu Leu Glu Leu Met
        1540                1545                1550

Gly Thr Arg Ala Gln Leu Leu Ala Ala Ser Arg Glu Leu His Lys Phe
    1555                1560                1565

Phe Ser Asp Ala Arg Glu Leu Gln Gly Gln Ile Glu Glu Lys Arg Arg
    1570                1575                1580

Arg Leu Pro Arg Leu Thr Thr Pro Pro Glu Pro Arg Pro Ser Ala Ser
1585                1590                1595                1600

Ser Met Gln Arg Thr Leu Arg Ala Phe Glu His Asp Leu Gln Leu Leu
        1605                1610                1615

Val Ser Gln Val Arg Gln Leu Gln Glu Gly Ala Ala Gln Leu Arg Thr
        1620                1625                1630

Val Tyr Ala Gly Glu His Ala Glu Ala Ile Ala Ser Arg Glu Gln Glu
        1635                1640                1645

Val Leu Gln Gly Trp Lys Glu Leu Leu Ser Ala Cys Glu Asp Ala Arg
    1650                1655                1660

Leu His Val Ser Ser Thr Ala Asp Ala Leu Arg Phe His Ser Gln Val

-continued

```
              1665                1670                1675                1680

Arg Asp Leu Leu Ser Trp Met Asp Gly Ile Ala Ser Gln Ile Gly Ala
                    1685                1690                1695

Ala Asp Lys Pro Arg Asp Val Ser Val Glu Val Leu Met Asn Tyr
        1700                1705                1710

His Gln Gly Leu Lys Thr Glu Leu Glu Ala Arg Val Pro Glu Leu Thr
            1715                1720                1725

Thr Cys Gln Glu Leu Gly Arg Ser Leu Leu Asn Lys Ser Ala Met
        1730                1735                1740

Ala Asp Glu Ile Gln Ala Gln Leu Asp Lys Leu Gly Thr Arg Lys Glu
1745                1750                1755                1760

Glu Val Ser Glu Lys Trp Asp Arg His Trp Glu Trp Leu Gln Gln Met
                1765                1770                1775

Leu Glu Val His Gln Phe Ala Gln Glu Ala Val Val Ala Asp Ala Trp
            1780                1785                1790

Leu Thr Ala Gln Glu Pro Leu Leu Gln Ser Arg Glu Leu Gly Ser Ser
        1795                1800                1805

Val Asp Glu Val Glu Gln Leu Ile Arg Arg His Glu Ala Phe Arg Lys
        1810                1815                1820

Ala Ala Ala Ala Trp Glu Glu Arg Phe Ser Ser Leu Arg Arg Leu Thr
1825                1830                1835                1840

Thr Ile Glu Lys Ile Lys Ala Glu Gln Ser Lys Gln Pro Thr Pro
                1845                1850                1855

Leu Leu Gly Arg Lys Phe Phe Gly Asp Pro Thr Glu Leu Ala Ala Lys
            1860                1865                1870

Ala Ala Pro Leu Leu Arg Pro Gly Gly Tyr Glu Arg Gly Leu Glu Pro
        1875                1880                1885

Leu Ala Arg Arg Ala Ser Asp Thr Leu Ser Ala Glu Val Arg Thr Arg
        1890                1895                1900

Val Gly Tyr Val Arg Gln Glu Leu Lys Pro Glu Arg Leu Gln Pro Arg
1905                1910                1915                1920

Ile Asp Arg Leu Pro Glu Ile Pro Gly Arg Val Glu Pro Ala Ala Leu
                1925                1930                1935

Pro Ala Ala Pro Glu Asp Ala Ala Glu Thr Pro Ala Thr Pro Ala Ala
            1940                1945                1950

Ala Glu Gln Val Arg Pro Arg Pro Glu Arg Gln Glu Ser Ala Asp Arg
        1955                1960                1965

Ala Glu Glu Leu Pro Arg Arg Arg Pro Glu Arg Gln Glu Ser Val
        1970                1975                1980

Asp Gln Ser Glu Glu Ala Ala Arg Arg Arg Pro Glu Arg Gln Glu
1985                1990                1995                2000

Ser Ala Glu His Glu Ala Ala His Ser Leu Thr Leu Gly Arg Tyr Glu
                2005                2010                2015

Gln Met Glu Arg Arg Arg Glu Arg Arg Glu Arg Arg Leu Glu Arg Gln
            2020                2025                2030

Glu Ser Ser Glu Gln Glu Met Pro Ile Arg Gly Asp Leu Val Lys Gly
        2035                2040                2045

Lys Ala Thr Leu Ala Asp Ile Val Glu Gln Leu Gln Glu Lys Glu Ala
2050                2055                2060

Gly Pro Gly Leu Pro Ala Gly Pro Ser Leu Pro Gln Pro Arg Glu Leu
2065                2070                2075                2080

Pro Pro Gly Arg Leu Pro Asn Gly Leu Glu Leu Pro Glu Arg Thr Pro
                2085                2090                2095
```

-continued

```
Arg Pro Asp Arg Pro Arg Ala Arg Asp Arg Pro Lys Pro Arg Arg
            2100                2105                2110
Pro Arg Pro Arg Glu Gly Gly Glu Gly Gly Gly Ser Arg Arg Ser Arg
            2115                2120                2125
Ser Ala Pro Ala Gln Gly Gly Ser Ala Pro Ala Pro Pro Pro Pro
            2130                2135                2140
Thr His Thr Val Gln His Glu Gly Phe Leu Leu Arg Lys Arg Glu Leu
2145                2150                2155                2160
Asp Ala Asn Arg Lys Ser Ser Asn Arg Ser Trp Val Ser Leu Tyr Cys
            2165                2170                2175
Val Leu Ser Lys Gly Glu Leu Gly Phe Tyr Lys Asp Ser Lys Gly Pro
            2180                2185                2190
Ala Ser Gly Ser Thr His Gly Gly Glu Pro Leu Leu Ser Leu His Lys
            2195                2200                2205
Ala Thr Ser Glu Val Ala Ser Asp Tyr Lys Lys Lys His Val Phe
            2210                2215                2220
Lys Leu Gln Thr Gln Asp Gly Ser Glu Phe Leu Leu Gln Ala Lys Asp
2225                2230                2235                2240
Glu Glu Glu Met Asn Gly Trp Leu Glu Ala Val Ala Ser Ser Val Ala
            2245                2250                2255
Glu His Ala Glu Ile Ala Arg Trp Gly Gln Thr Leu Pro Thr Thr Ser
            2260                2265                2270
Ser Thr Asp Glu Gly Asn Pro Lys Arg Glu Gly Asp Arg Arg Ala
            2275                2280                2285
Ser Gly Arg Arg Lys
    2290

<210> SEQ ID NO 3
<211> LENGTH: 5
<212> TYPE: PRT
<213> ORGANISM: Human

<400> SEQUENCE: 3

Glu Arg Asn Glu Ser
 1               5

<210> SEQ ID NO 4
<211> LENGTH: 29
<212> TYPE: DNA
<213> ORGANISM: Artificial Sequence
<220> FEATURE:
<223> OTHER INFORMATION: 5' primer sequence

<400> SEQUENCE: 4
cctcagctgg ccggacgagg gcacaccgg                                    29

<210> SEQ ID NO 5
<211> LENGTH: 29
<212> TYPE: DNA
<213> ORGANISM: Artificial Sequence
<220> FEATURE:
<223> OTHER INFORMATION: 3' primer sequence

<400> SEQUENCE: 5
ccggtgtgcc ctcgtccggc cagctgagg                                    29

<210> SEQ ID NO 6
<211> LENGTH: 27
<212> TYPE: DNA
```

```
<213> ORGANISM: Artificial Sequence
<220> FEATURE:
<223> OTHER INFORMATION: 5' primer sequence

<400> SEQUENCE: 6
cgtgcactgc tcggccggtg cggggag                                          27

<210> SEQ ID NO 7
<211> LENGTH: 26
<212> TYPE: DNA
<213> ORGANISM: Artificial Sequence
<220> FEATURE:
<223> OTHER INFORMATION: 3' primer sequence

<400> SEQUENCE: 7
ctccccgcac cggccgagca gtgcac                                           26

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide for Antibody preparation

<400> SEQUENCE: 8

Cys Glu Glu Leu Pro Arg Arg Arg Arg Pro Glu Arg Gln Glu Ser Val
 1               5                  10                  15

Asp Gln Ser Glu Glu
            20
```

What is claimed is:

1. An isolated nucleic acid comprising a sequence that encodes a polypeptide with the amino acid sequence of SEQ ID NO:2.

2. The isolated nucleic acid of claim 1, wherein said isolated nucleic acid is DNA.

3. The isolated nucleic acid of claim 1, wherein said isolated nucleic acid is RNA.

4. The isolated nucleic acid of claim 1, wherein said isolated nucleic acid comprises the nucleic acid sequence of SEQ ID NO:1.

5. The isolated nucleic acid of claim 1, wherein said polypeptide binds to an autoantigen of type I diabetes.

6. The isolated nucleic acid of claim 5, wherein said autoantigen of type I diabetes is ICA512.

7. The isolated nucleic acid of claim 5, wherein said autoantigen of type I diabetes is the cytoplasmic domain of ICA512.

8. The isolated nucleic acid of claim 5, wherein said autoantigen of type I diabetes is phogrin.

9. The isolated nucleic acid of claim 1, wherein said isolated nucleic acid is derived from a gene in human chromosome 19q13.13.

* * * * *